United States Patent
Cahoon et al.

(10) Patent No.: US 6,680,185 B1
(45) Date of Patent: Jan. 20, 2004

(54) PLANT POLYPHENOL OXIDASE HOMOLOGS

(75) Inventors: Rebecca E. Cahoon, Wilmington, DE (US); Saverio Carl Falco, Arden, DE (US); Anthony J. Kinney, Wilmington, DE (US); Guo-Hua Miao, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/889,463

(22) PCT Filed: Feb. 8, 2000

(86) PCT No.: PCT/US00/03176

§ 371 (c)(1),
(2), (4) Date: Jul. 16, 2001

(87) PCT Pub. No.: WO00/47726

PCT Pub. Date: Aug. 17, 2000

Related U.S. Application Data

(60) Provisional application No. 60/119,590, filed on Feb. 10, 1999.

(51) Int. Cl.$^7$ .............................. C12N 9/04; C12N 1/20; C12N 15/00; C12P 21/04; C07H 21/04
(52) U.S. Cl. .................... 435/190; 435/183; 435/252.3; 435/320.1; 435/71.1; 536/23.2; 536/23.1
(58) Field of Search ................................ 435/190, 183, 435/252.3, 320.1, 71.1; 536/23.2, 23.1

(56) References Cited

U.S. PATENT DOCUMENTS 5,786,193 A * 7/1998 Greene et al. .............. 435/193

FOREIGN PATENT DOCUMENTS

| WO | 93/02195 A1 | 2/1993 |
| WO | 93/15599 A1 | 8/1993 |
| WO | 97/29193 A1 | 8/1997 |
| WO | 98/53080 A1 | 11/1998 |

OTHER PUBLICATIONS

Michelle D. Hunt, et. al., Plant Molecular Biology, vol. 21:59–68, 1993, cDNA Cloning and Expression of Potato Polyphenol Oxidase.
Sally M. Newman, et. al., Plant Molecular Biology, vol. 21:1035–1051, 1993, Organisation of the Tomato Polyphenol Oxidase Gene Family.
National Center for Biotechnology Information General Identifier No. 1172584, Oct. 1, 1996, Boss, P.K., et al., an Apple Polyphenol Oxidase cDNA is Up–Regulated in Wounded Tissues.
Paul K. Boss, et. al., Plant Molecular Biology, vol. 27:429–433, 1995, an Apple Polyphenol Oxidase cDNA is Up–Regulated in Wounded Tissues.
National Center for Biotechnology Information General Identifier No. 1785613, Jan. 18, 1997, Virador, V.M., et. al., Molecular Cloning and c–DNA Sequence of Grenache (Vitis Vinifera) Leaf Polyphenol Oxidase.
National Center for Biotechnology Information General Identifier No. 418754, Jul. 21, 2000, Cary, J.W., et. al., Cloning and Characterization of cDNAS Coding for Vicia Faba Polyphenol Oxidase.
Jeffrey W. Cary, et. al., Plant Molecular Biology, vol. 20:245–253, 1992, Cloning and Characterization of cDNAS Coding for Vicia Faba Polyphenol Oxidase.
National Center for Biotechnology Information General Identifier No. 1172586, Dec. 15, 1998, Cary, J.W., et. al., Cloning and Characterization of cDNAS Coding for Vicia Faba Polyphenol Oxidase.
William H. Flurkey, Plant Phys., VOL 91:481–483, 1989, Polypeptide Composition and Amino–Terminal Sequence of Broad Bean Polyphenoloxidase.
National Center for Biotechnology Information General Identifier No. 451937, Jun. 4, 1999, Haruta,M., et. al., Immunological and Molecular Comparison of Polyphenol Oxidase in Rosaceae Fruit Trees.
Miyoshi Haruta, et. al., Phytochemistry, vol. 50:1021–1025, 1999, Immunological and Molecular Comparison of Polyphenol Oxidase in Rosaceae Fruit Trees.
National Center for Biotechnology Information General Identifier No. 2737882, Jan. 1, 1998, Bucheli, C.S., et. al., Purification of Polyphenol Oxidase and Isolation of a Full Length cDNA from Sugarcane, a C4 Grass.

* cited by examiner

Primary Examiner—Ponnathapu Achutamurthy
Assistant Examiner—Yong Pak

(57) ABSTRACT

This invention relates to an isolated nucleic acid fragment encoding a polyphenol oxidase enzyme. The invention also relates to the construction of a chimeric gene encoding all or a portion of the polyphenol oxidase enzyme, in sense or antisense orientation, wherein expression of the chimeric gene results in production of altered levels of the polyphenol oxidase enzyme in a transformed host cell.

11 Claims, No Drawings

SEQUENCE LISTING

```
<160> NUMBER OF SEQ ID NOS: 46

<210> SEQ ID NO 1
<211> LENGTH: 512
<212> TYPE: DNA
<213> ORGANISM: Zea mays
<220> FEATURE:
<221> NAME/KEY: unsure
<222> LOCATION: (489)
<223> OTHER INFORMATION: n = a, c, g or t
<220> FEATURE:
<221> NAME/KEY: unsure
<222> LOCATION: (510)
<223> OTHER INFORMATION: n = a, c, g or t

<400> SEQUENCE: 1
ggacatggcc tccatttcgc atttaattgc taagccagct ccagctgcca cctttcctct      60 atccctccg  agaacgagct ccggcttcag gcctcgccgc gttaccgtcc agcgcgtctc     120
gtgcgcatct cccagaggcg aacgctccga gccagacgcc caaaagcacg accgccgcga     180
cgtcctcctc ggcctcggag cgctcggtgc cagtgccacc gctaccctgg cgtccgcgcg     240
ccgcgccggc gccgaccccg tcgccacgcc cgacatctct tcctgcggcc aagcgaacct     300
tccggtgagc gccaacgtgc tgacgtgctg cccgccgccc tcgagcgcgc tgcccgtgga     360
cttcatcctc cccgacgcca cgtccttgcc gctccggacg cgcccgccg  cgcactcggt     420 caccacggac tacgtcgcca aagttcaacg ccgggatcgc tgcgatgaag gggctcccgg     480
cgggacganc cgcgtagctt cgcggcgcan gg                                  512

<210> SEQ ID NO 2
<211> LENGTH: 150
<212> TYPE: PRT
<213> ORGANISM: Zea mays

<400> SEQUENCE: 2

Met Ala Ser Ile Ser His Leu Ile Ala Lys Pro Ala Pro Ala Ala Thr
 1               5                  10                  15

Phe Pro Leu Ser Leu Pro Arg Thr Ser Ser Gly Phe Arg Pro Arg Arg
```

|  |  |  | 20 |  |  |  | 25 |  |  |  | 30 |  |
|---|---|---|---|---|---|---|---|---|---|---|---|---|
| Val | Thr | Val | Gln | Arg | Val | Ser | Cys | Ala | Ser | Pro | Arg | Gly | Glu | Arg | Ser |
|  |  | 35 |  |  |  |  | 40 |  |  |  |  | 45 |

Glu Pro Asp Ala Gln Lys His Asp Arg Arg Asp Val Leu Leu Gly Leu
         50                  55                  60

Gly Ala Leu Gly Ala Ser Ala Thr Ala Thr Leu Ala Ser Ala Arg Arg
 65                  70                  75                  80

Ala Gly Ala Asp Pro Val Ala Thr Pro Asp Ile Ser Ser Cys Gly Gln
                 85                  90                  95

Ala Asn Leu Pro Val Ser Ala Asn Val Leu Thr Cys Cys Pro Pro Pro
             100                 105                 110

Ser Ser Ala Leu Pro Val Asp Phe Ile Leu Pro Asp Ala Thr Ser Leu
         115                 120                 125

Pro Leu Arg Thr Arg Pro Ala Ala His Ser Val Thr Thr Asp Tyr Val
     130                 135                 140

Ala Lys Val Gln Arg Arg
145                 150

<210> SEQ ID NO 3
<211> LENGTH: 995
<212> TYPE: DNA
<213> ORGANISM: Zea mays

<400> SEQUENCE: 3

```
gcacgaggga catggcctcc atttcgcatt taattgctaa gccagctcca gctgccacct    60
ttcctctatc ccttccgaga acgagctccg gcttcaggcc tcgccgcgtt accgtccagc   120
gcgtctcgtg cgcatctccc agaggcgaac gctccgagcc agacgcccaa agcacgacc    180
gccgcgacgt cctcctcggc ctcggagcgc tcggtgccag tgccaccgct accctggcgt   240
ccgcgcgccg cgccggcgcc gaccccgtcg ccacgcccga catctcttcc tgcggccaag   300
cgaaccttcc ggtgagcgcc aacgtgctga cgtgctgccc gccgccctcg agcgcgctgc   360
ccgtggactt catcctcccc gacgccacgt ccttgccgct ccggacgcgc ccgccgcgc    420
actcggtcac cacggactac gtcgccaagt tcaacgccgg gatcgctgcg atgaaggcgc   480
tcccggcgga cgacccgcgt agcttcgcgg cgcaggcgag cgtgcactgc gcctactgcg   540
acgggtcgta cagccccgag gggttccccg gtgtggagct ccaggtgcac aactcgtggc   600
tcttttttccc cttccaccgc tgctaccatt acttcttcga gcgcatcctg ggcagcctga   660
tcggcgaccc cggcttcgcg gtaccgttct ggaactggga cgcgccggac gggatgcgca   720
tgccggccat gtacgcggac cggtcatccc agctgttcga tccgcggcgt gacagccggc   780
acgcgccgcc gaagctcatc aatctggact acaacgccaa cgttagggag ccgaggttca   840
cttactaaca acaggttgat cacaacctca gggtcatgta ccgtcaggta attaacaacg   900
tgtgtttaca tgctatgaag tatgaactgc cgaaaccaag tacatggtct tggaatcttg   960
ccaaaactga tcaaaaaaaa aaaaaaaaaa aaaaa                              995
```

<210> SEQ ID NO 4
<211> LENGTH: 278
<212> TYPE: PRT
<213> ORGANISM: Zea mays

<400> SEQUENCE: 4

Met Ala Ser Ile Ser His Leu Ile Ala Lys Pro Ala Pro Ala Ala Thr
 1               5                  10                  15

```
Phe Pro Leu Ser Leu Pro Arg Thr Ser Ser Gly Phe Arg Pro Arg Arg
             20                  25                  30

Val Thr Val Gln Arg Val Ser Cys Ala Ser Pro Arg Gly Glu Arg Ser
         35                  40                  45

Glu Pro Asp Ala Gln Lys His Asp Arg Arg Asp Val Leu Leu Gly Leu
     50                  55                  60

Gly Ala Leu Gly Ala Ser Ala Thr Ala Thr Leu Ala Ser Ala Arg Arg
 65                  70                  75                  80

Ala Gly Ala Asp Pro Val Ala Thr Pro Asp Ile Ser Ser Cys Gly Gln
                 85                  90                  95

Ala Asn Leu Pro Val Ser Ala Asn Val Leu Thr Cys Cys Pro Pro Pro
            100                 105                 110

Ser Ser Ala Leu Pro Val Asp Phe Ile Leu Pro Asp Ala Thr Ser Leu
            115                 120                 125

Pro Leu Arg Thr Arg Pro Ala Ala His Ser Val Thr Thr Asp Tyr Val
        130                 135                 140

Ala Lys Phe Asn Ala Gly Ile Ala Ala Met Lys Ala Leu Pro Ala Asp
145                 150                 155                 160

Asp Pro Arg Ser Phe Ala Ala Gln Ala Ser Val His Cys Ala Tyr Cys
                165                 170                 175

Asp Gly Ser Tyr Ser Pro Glu Gly Phe Pro Gly Val Glu Leu Gln Val
            180                 185                 190

His Asn Ser Trp Leu Phe Phe Pro Phe His Arg Cys Tyr Leu Tyr Phe
        195                 200                 205

Phe Glu Arg Ile Leu Gly Ser Leu Ile Gly Asp Pro Gly Phe Ala Val
        210                 215                 220

Pro Phe Trp Asn Trp Asp Ala Pro Asp Gly Met Arg Met Pro Ala Met
225                 230                 235                 240

Tyr Ala Asp Arg Ser Ser Gln Leu Phe Asp Pro Arg Arg Asp Ser Arg
                245                 250                 255

His Ala Pro Pro Lys Leu Ile Asn Leu Asp Tyr Asn Ala Asn Val Arg
            260                 265                 270

Glu Pro Arg Phe Thr Tyr
        275

<210> SEQ ID NO 5
<211> LENGTH: 403
<212> TYPE: DNA
<213> ORGANISM: Zea mays
<220> FEATURE:
<221> NAME/KEY: unsure
<222> LOCATION: (347)
<223> OTHER INFORMATION: n = a, c, g or t
<220> FEATURE:
<221> NAME/KEY: unsure
<222> LOCATION: (352)
<223> OTHER INFORMATION: n = a, c, g or t
<220> FEATURE:
<221> NAME/KEY: unsure
<222> LOCATION: (360)
<223> OTHER INFORMATION: n = a, c, g or t
<220> FEATURE:
<221> NAME/KEY: unsure
<222> LOCATION: (399)
<223> OTHER INFORMATION: n = a, c, g or t
<220> FEATURE:
<221> NAME/KEY: unsure
<222> LOCATION: (401)
<223> OTHER INFORMATION: n = a, c, g or t

<400> SEQUENCE: 5
```

-continued

| | |
|---|---|
| ggaacggcct ccgccccggc aacagcgact tcaccgaccc cagctggctg gacgccagct | 60 |
| tcctcttcta cgacgaggag gcccgcctcg tccgcgtgcg cgtccgggac tgcctcgaca | 120 |
| ccgctgccct gggctacgcc taccaggacg tcgccctgcc gtggctgaac gccaagccgg | 180 |
| ccaaggaggc cgggtctccg gcgcccaccg cgggcgcgct cccggcgaca ctgaaccaga | 240 |
| ccgtgcgggt ggccgtgacg cggcccaaga cctcgaggac ccgcaaggag aaggacgcca | 300 |
| aggaagaagt gctggtcgtc caagggatcg aaatcgctga ccactcnaac angttcgtcn | 360 |
| agttcgactt gttcgtgaac gaatcccaaa acgggggcng nat | 403 |

<210> SEQ ID NO 6
<211> LENGTH: 126
<212> TYPE: PRT
<213> ORGANISM: Zea mays
<220> FEATURE:
<221> NAME/KEY: UNSURE
<222> LOCATION: (117)
<223> OTHER INFORMATION: Xaa = any amino acid
<220> FEATURE:
<221> NAME/KEY: UNSURE
<222> LOCATION: (120)
<223> OTHER INFORMATION: Xaa = any amino acid

<400> SEQUENCE: 6

Asn Gly Leu Arg Pro Gly Asn Ser Asp Phe Thr Asp Pro Ser Trp Leu
 1               5                  10                  15

Asp Ala Ser Phe Leu Phe Tyr Asp Glu Glu Ala Arg Leu Val Arg Val
            20                  25                  30

Arg Val Arg Asp Cys Leu Asp Thr Ala Ala Leu Gly Tyr Ala Tyr Gln
        35                  40                  45

Asp Val Ala Leu Pro Trp Leu Asn Ala Lys Pro Ala Lys Glu Ala Gly
    50                  55                  60

Ser Pro Ala Pro Thr Ala Gly Ala Leu Pro Ala Thr Leu Asn Gln Thr
65                  70                  75                  80

Val Arg Val Ala Val Thr Arg Pro Lys Thr Ser Arg Thr Arg Lys Glu
                85                  90                  95

Lys Asp Ala Lys Glu Glu Val Leu Val Val Gln Gly Ile Glu Ile Ala
            100                 105                 110

Asp His Ser Asn Xaa Phe Val Xaa Phe Asp Leu Phe Val Asn
        115                 120                 125

<210> SEQ ID NO 7
<211> LENGTH: 711
<212> TYPE: DNA
<213> ORGANISM: Glycine max
<220> FEATURE:
<221> NAME/KEY: unsure
<222> LOCATION: (573)
<223> OTHER INFORMATION: n = a, c, g or t
<220> FEATURE:
<221> NAME/KEY: unsure
<222> LOCATION: (602)
<223> OTHER INFORMATION: n = a, c, g or t
<220> FEATURE:
<221> NAME/KEY: unsure
<222> LOCATION: (669)
<223> OTHER INFORMATION: n = a, c, g or t

<400> SEQUENCE: 7

| | |
|---|---|
| tttttttttt tttttcatt ggacaaccaa cattattatt ataacattat ggagatgcag | 60 |
| atcatcatca tcccactagg gagtatactt tctcgtgccg aattcggcac ctcagtcatt | 120 |
| cgtgtctgca gtgtataatg ttccttccaa gtctaccact ctcccttctt ccctgcatcc | 180 |

-continued

```
atttttcacaa tcccaatcca ctaaatatag aaaatcaaaa caccatcaca ctcctagagt      240
gacatgtaat agtggaaacc aaaacaaagg agaaaaacca gatattcata tagaacaaag      300
gaggaacatt ctacttggcc taggagggct ttgtggtgct gctactctta acaacaaccc      360
ttttgcattt gctgcgccaa tatctcctcc aagacctaac acatgtggtc caccagacct      420
acctgaaggt gcagaaccca caaattgttg cccccccattt tcatccacca tcatagatttt     480 caagtttcct ccttctaaca aacccttgcg tgtaagacca gctgcacatt tagttgacaa      540
aaattatcta gccaaataca aaaagccat tgncctcatg aaaaattcca gctaacgatc      600
anctatttca tcaacaagca aacgtgcacg cgctatgcac tggttaaatg acaaattggg      660
tcctggccnt gagctcagtg caagctctgg cctcttccta cacgatggtc t                711
```

<210> SEQ ID NO 8
<211> LENGTH: 156
<212> TYPE: PRT
<213> ORGANISM: Glycine max
<220> FEATURE:
<221> NAME/KEY: UNSURE
<222> LOCATION: (153)
<223> OTHER INFORMATION: Xaa = any amino acid

<400> SEQUENCE: 8

```
Ser Phe Val Ser Ala Val Tyr Asn Val Pro Ser Lys Ser Thr Thr Leu
 1               5                  10                  15

Pro Ser Ser Leu His Pro Phe Ser Gln Ser Gln Ser Thr Lys Tyr Arg
            20                  25                  30

Lys Ser Lys His His His Thr Pro Arg Val Thr Cys Asn Ser Gly Asn
        35                  40                  45

Gln Asn Lys Gly Glu Lys Pro Asp Ile His Ile Glu Gln Arg Arg Asn
    50                  55                  60

Ile Leu Leu Gly Leu Gly Gly Leu Cys Gly Ala Ala Thr Leu Asn Asn
65                  70                  75                  80

Asn Pro Phe Ala Phe Ala Ala Pro Ile Ser Pro Pro Arg Pro Asn Thr
                85                  90                  95

Cys Gly Pro Pro Asp Leu Pro Glu Gly Ala Glu Pro Thr Asn Cys Cys
            100                 105                 110

Pro Pro Phe Ser Ser Thr Ile Ile Asp Phe Lys Phe Pro Pro Ser Asn
        115                 120                 125

Lys Pro Leu Arg Val Arg Pro Ala Ala His Leu Val Asp Lys Asn Tyr
    130                 135                 140

Leu Ala Lys Tyr Lys Lys Ala Ile Xaa Leu Met Lys
145                 150                 155
```

<210> SEQ ID NO 9
<211> LENGTH: 2485
<212> TYPE: DNA
<213> ORGANISM: Glycine max

<400> SEQUENCE: 9

```
gcacgagttt tttttttttt tttcattgga caaccaacat tattattata acattatgga       60
gatgcagatc atcatcatcc cactagggag tatactttct cgtgccgaat cggcacctc       120 agtcattcgt gtctgcagtg tataatgttc cttccaagtc taccactctc ccttcttccc      180
tgcatccatt ttcacaatcc caatccacta aatatagaaa atcaaaacac catcacactc      240
ctagagtgac atgtaatagt ggaaaccaaa acaaggaga aaaccagat attcatatag       300
```

-continued

```
aacaaaggag gaacattcta cttggcctag gagggctttg tggtgctgct actcttaaca    360
acaacccttt tgcatttgct gcgccaatat ctcctccaga cctaaccaca tgtggtccac    420
cagacctacc tgaaggtgca gaacccacaa attgttgccc cccattttca tccaccatca    480
tagatttcaa gtttcctcct tctaacaaac ctttgcgtgt aagaccagct gcacatttag    540
ttgacaaaaa ttatctagcc aaatacaaaa agccattga cctcatgaaa aaactcccag     600
ctaacgatcc acgcaatttc atgcaacaag caaacgtgca ctgcgcttat tgcactggtt    660
catatgacca agttgggttc cctggccttg agctccaagt gcacagctct ggctcttct    720
ttccctacca ccgatggttc ctctatttct atgagagaat tttggggagc ttgatcaatg    780
atccaacatt tgcccttcca ttttggaact gggatgctcc taagggcatg caacttcctt    840
ccatttatgc agaccccaaa tcacctcttt atgaccctct tcgcaatgcg aatcaccaac    900
ctccaacact tgtggacttt gacttcaatc ttgacaatcc tatttccaat ggaagaatct    960
ccaccaacct caccataatg tataggcaac ttgtgtctaa tggaaaaact cctactttgt   1020
tccttggaaa tccttatcgt gccggggatg cgcctgaccc tggcggtggc tcagtagagg   1080
gcgttccaca tggtccggtt catctatgga caggtgatat aaatcaacca acattgaga   1140
acatggggga tttctattct gctgcaagag atcctatttt ctattctcac cattccaatg   1200
ttgataggat gtggtctata tggaaaacac ttggtgggaa gagaagggat ttcaccgact   1260
cagattggtt ggaatctggg ctcctcttct acgatgagaa taagaacctt gtgcgtgtga   1320
aggtcaagga ttgtcttgac acaagaaagc taggatatgt ttaccaagat gttgaaattc   1380
catggttaaa atctaagcct tcaccgcgta ggtcgagggt tcaaaaggta gcactaggac   1440
cacattttaa tactggtgta gcacgtgctg ctgagacttc gaggaatgtt cagttcccat   1500
tggtgttgga ttcagttgtg agcatagtgg tgaagaggcc aaaaaagtcg aggagcaaga   1560
aggagaagga agaggaagag gaggttcttg tgattgaagg ggttgagtat gacagcaaca   1620
taccagtgaa atttgatgtg cttattaatg atgaagatga taagcagatt cagccagaag   1680
attcggagta tgcaggaagc tttgtgactg tgcctcattc gcataagcac aaaaataaga   1740
agattatcac ttgtttgagg ctgggactga cagatttgtt ggaagaattg gaagcagaag   1800
atgatgatag tgttgtggtg acgttggttc cgaggtatgg gaaagggcgt gtccaaattg   1860
gaggcatcaa gatagatctt gttgcagatt aaaaaatatt tatatacttc gactgtttaa   1920
cctcataata atatatatat atatatatat aatgtagttt cttggatttg tgtttgcttt   1980
tatatgaaaa atgtagtttt tgttatgtat tttccatgag aatcataaga atgtcgctaa   2040
ttgaagtgaa aaaaaaaaaa aaaaaaaaaa aaaaaaaaaa aaaaaaaaaa aaaaaaaaaa   2100
aaaaaaaacc cccgggggggg ggccgggaac aaaatccccc aaaaagagag tcataaaacg   2160
cgcgcacagg ggccgtcttt taaaaacctc gaaagggaaa aaacccgggc gaaacaaaat   2220
aaaaacccctt taaaaaaaac ccccctttcc aaaagggaaa aaaaaaaaa aaggcccaca   2280
acaatccccc tccaaaaaaa tttgcccacc caaaagggaa aaggagaccc ccctgtagc    2340
ggcaaaaaaa ccgggggggg tgtggggggat acccaaatgt aaccgaaaaa tttgaaaacc   2400
ccaaagcccc cgcccctttc cttttctccc cttcctttcc ccaaatttcc cgggtttccc   2460
ccgaaaaacc aaaaaacggg ggccc                                         2485
```

<210> SEQ ID NO 10
<211> LENGTH: 601
<212> TYPE: PRT
<213> ORGANISM: Glycine max

<400> SEQUENCE: 10

```
Gly Val Tyr Phe Leu Val Pro Asn Ser Ala Pro Gln Ser Phe Val Ser
  1               5                  10                  15

Ala Val Tyr Asn Val Pro Ser Lys Ser Thr Thr Leu Pro Ser Ser Leu
                 20                  25                  30

His Pro Phe Ser Gln Ser Gln Ser Thr Lys Tyr Arg Lys Ser Lys His
             35                  40                  45

His His Thr Pro Arg Val Thr Cys Asn Ser Gly Asn Gln Asn Lys Gly
         50                  55                  60

Glu Lys Pro Asp Ile His Ile Glu Gln Arg Arg Asn Ile Leu Leu Gly
 65                  70                  75                  80

Leu Gly Gly Leu Cys Gly Ala Ala Thr Leu Asn Asn Asn Pro Phe Ala
                 85                  90                  95

Phe Ala Ala Pro Ile Ser Pro Pro Asp Leu Thr Thr Cys Gly Pro Pro
                100                 105                 110

Asp Leu Pro Glu Gly Ala Glu Pro Thr Asn Cys Cys Pro Pro Phe Ser
            115                 120                 125

Ser Thr Ile Ile Asp Phe Lys Phe Pro Pro Ser Asn Lys Pro Leu Arg
        130                 135                 140

Val Arg Pro Ala Ala His Leu Val Asp Lys Asn Tyr Leu Ala Lys Tyr
145                 150                 155                 160

Lys Lys Ala Ile Asp Leu Met Lys Lys Leu Pro Ala Asn Asp Pro Arg
                165                 170                 175

Asn Phe Met Gln Gln Ala Asn Val His Cys Ala Tyr Cys Thr Gly Ser
            180                 185                 190

Tyr Asp Gln Val Gly Phe Pro Gly Leu Glu Leu Gln Val His Ser Ser
        195                 200                 205

Trp Leu Phe Phe Pro Tyr His Arg Trp Phe Leu Tyr Phe Tyr Glu Arg
    210                 215                 220

Ile Leu Gly Ser Leu Ile Asn Asp Pro Thr Phe Ala Leu Pro Phe Trp
225                 230                 235                 240

Asn Trp Asp Ala Pro Lys Gly Met Gln Leu Pro Ser Ile Tyr Ala Asp
                245                 250                 255

Pro Lys Ser Pro Leu Tyr Asp Pro Leu Arg Asn Ala Asn His Gln Pro
            260                 265                 270

Pro Thr Leu Val Asp Phe Asp Phe Asn Leu Asp Asn Pro Ile Ser Asn
        275                 280                 285

Gly Arg Ile Ser Thr Asn Leu Thr Ile Met Tyr Arg Gln Leu Val Ser
    290                 295                 300

Asn Gly Lys Thr Pro Thr Leu Phe Leu Gly Asn Pro Tyr Arg Ala Gly
305                 310                 315                 320

Asp Ala Pro Asp Pro Gly Gly Gly Ser Val Glu Gly Val Pro His Gly
                325                 330                 335

Pro Val His Leu Trp Thr Gly Asp Ile Asn Gln Pro Asn Ile Glu Asn
            340                 345                 350

Met Gly Asp Phe Tyr Ser Ala Ala Arg Asp Pro Ile Phe Tyr Ser His
        355                 360                 365

His Ser Asn Val Asp Arg Met Trp Ser Ile Trp Lys Thr Leu Gly Gly
    370                 375                 380

Lys Arg Arg Asp Phe Thr Asp Ser Asp Trp Leu Glu Ser Gly Leu Leu
385                 390                 395                 400

Phe Tyr Asp Glu Asn Lys Asn Leu Val Arg Val Lys Val Lys Asp Cys
```

```
                        405                 410                 415
Leu Asp Thr Arg Lys Leu Gly Tyr Val Tyr Gln Asp Val Glu Ile Pro
                420                 425                 430
Trp Leu Lys Ser Lys Pro Ser Pro Arg Ser Arg Val Gln Lys Val
            435                 440                 445
Ala Leu Gly Pro His Phe Asn Thr Gly Val Ala Arg Ala Glu Thr
        450                 455                 460
Ser Arg Asn Val Gln Phe Pro Leu Val Leu Asp Ser Val Ser Ile
465                 470                 475                 480
Val Val Lys Arg Pro Lys Lys Ser Arg Ser Lys Lys Glu Lys Glu Glu
                485                 490                 495
Glu Glu Glu Val Leu Val Ile Glu Gly Val Tyr Asp Ser Asn Ile
                500                 505                 510
Pro Val Lys Phe Asp Val Leu Ile Asn Asp Glu Asp Lys Gln Ile
                515                 520                 525
Gln Pro Glu Asp Ser Glu Tyr Ala Gly Ser Phe Val Thr Val Pro His
            530                 535                 540
Ser His Lys His Lys Asn Lys Lys Ile Ile Thr Cys Leu Arg Leu Gly
545                 550                 555                 560
Leu Thr Asp Leu Leu Glu Glu Leu Glu Ala Glu Asp Asp Ser Val
                565                 570                 575
Val Val Thr Leu Val Pro Arg Tyr Gly Lys Gly Arg Val Gln Ile Gly
            580                 585                 590
Gly Ile Lys Ile Asp Leu Val Ala Asp
        595                 600
```

<210> SEQ ID NO 11
<211> LENGTH: 450
<212> TYPE: DNA
<213> ORGANISM: Triticum aestivum
<220> FEATURE:
<221> NAME/KEY: unsure
<222> LOCATION: (20)
<223> OTHER INFORMATION: n = a, c, g or t
<220> FEATURE:
<221> NAME/KEY: unsure
<222> LOCATION: (357)
<223> OTHER INFORMATION: n = a, c, g or t
<220> FEATURE:
<221> NAME/KEY: unsure
<222> LOCATION: (389)
<223> OTHER INFORMATION: n = a, c, g or t
<220> FEATURE:
<221> NAME/KEY: unsure
<222> LOCATION: (412)
<223> OTHER INFORMATION: n = a, c, g or t
<220> FEATURE:
<221> NAME/KEY: unsure
<222> LOCATION: (444)
<223> OTHER INFORMATION: n = a, c, g or t

<400> SEQUENCE: 11

```
ctggtgccga attcggcacn agaccatttt acctcctcga gttcaccatg gagatcagca    60
cgagcgtggc aaggtgcact cgcatgccgt gcagcctcca agccctcgtg cccacgaagg   120
cgaggcagac gcggcgcctg acgtgcaagg caaccggcgg ccgcgtcgac cgccgcgacg   180
tgctcctcgg cctcggcagc gccgcggcgg ccgggctggg cgcgcagcgg ggccgagggg   240
cgattgccgc gcccatccag gccccggacc tcggcaactg caaccgcccc gacctcccga   300
acacggcgcc tgacaacaac tgctgcccga cgtccggcac cggcatcatc gacttcntgt   360
gccgccggct cctcgggcgc cgctccgcnt gcgcccggcc gcgcactggg anacgcggag   420
```

```
tactggccaa gtacaacggc cgtnggctaa                                      450
```

<210> SEQ ID NO 12
<211> LENGTH: 166
<212> TYPE: PRT
<213> ORGANISM: Triticum aestivum
<220> FEATURE:
<221> NAME/KEY: UNSURE
<222> LOCATION: (163)
<223> OTHER INFORMATION: Xaa = any amino acid

<400> SEQUENCE: 12

```
Met Glu Ile Ser Thr Ser Val Ala Arg Cys Thr Arg Met Pro Cys Ser
 1               5                  10                  15

Leu Gln Ala Leu Val Pro Thr Lys Ala Arg Gln Thr Arg Arg Leu Thr
             20                  25                  30

Cys Lys Ala Thr Gly Gly Arg Val Asp Arg Arg Asp Val Leu Leu Gly
         35                  40                  45

Leu Gly Ser Ala Ala Ala Ala Gly Leu Gly Ala Gln Arg Gly Arg Gly
     50                  55                  60

Ala Ile Ala Ala Pro Ile Gln Ala Pro Asp Leu Gly Asn Cys Asn Pro
 65                  70                  75                  80

Pro Asp Leu Pro Asn Thr Ala Pro Asp Thr Asn Cys Cys Pro Thr Ser
             85                  90                  95

Gly Thr Gly Ile Ile Asp Phe Val Leu Pro Pro Ala Pro Arg Ala Pro
        100                 105                 110

Leu Arg Val Arg Pro Ala Ala His Leu Ala Asp Ala Glu Tyr Leu Ala
    115                 120                 125

Lys Tyr Glu Arg Ala Val Ala Leu Met Lys Gln Leu Pro Ala Asp Asp
130                 135                 140

Pro Arg Ser Ser Lys Gln Gln Trp Arg Val His Cys Ala Tyr Cys Glu
145                 150                 155                 160

Arg Pro Xaa Arg Gln Val
                165
```

<210> SEQ ID NO 13
<211> LENGTH: 1993
<212> TYPE: DNA
<213> ORGANISM: Triticum aestivum

<400> SEQUENCE: 13

```
ctggtgccga attcggcacg agaccatttt acctcctcga gttcaccatg gagatcagca      60
cgagcgtggc aaggtgcact cgcatgccgt gcagcctcca agccctcgtg cccacgaagg     120
cgaggcagac gcggcgcctg acgtgcaagg caaccggcgg ccgcgtcgac cgccgcgacg     180
tgctcctcgg cctcggcagc gccgcggcgg ccgggctggg cgcgcagcgg gcccgagggg     240
cgattgccgc gcccatccag gccccggacc tcggcaactg caacccgccc gacctcccga     300
acacggcgcc tgacaccaac tgctgcccga cgtccggcac cggcatcatc gacttcgtgc     360
tgccgccggc ctcctcggcg ccgctccgcg tgcgcccggc cgcgcacctg gcagacgcgg     420
agtacctggc caagtacgag cgggccgtgg cgctcatgaa gcagctgccc gccgacgacc     480
cgcgcagctt cgagcagcag tggcgcgtgc actgcgccta ctgcgacggc gcctacgacc     540
aggtcggctt cccggacctg gagatccagg tgcacaactg ctggctcttc ttcccatggc     600
acaggttcta cctctacttc cacgagcgga tcctcggcaa gctcatcggc gacgacacct     660
tcgcgctgcc cttctggaac tgggacgcgc cggacggcat gacgctgccg gcgatctacg     720
```

-continued

```
ccaacaggtc gtcgccgctc tacaacgaga ggcgcaaccc cgcccaccag ccgccgttcc      780
cggtcgacct cgacttcaac gagatagatg tcatcatccc aacagacgag cagatcgacc      840
agaacctcaa catcatgtac cgccagatgg tgtcgggtgc caagaagact cggctgttca      900 tgggcagcc gtaccgcgcc ggcgaccagc cggaccctgg cgcgggctcc gtggagaacg       960
tgccgcacgg cacgatgcac acctggacgg gcgacccggc gcaacccaac aacgaggaca     1020
tgggcaactt ctactcggcg gcgcgcgacc ccatcttctt cgcgcaccac ggcaacatcg     1080
accgcctctg gcacgtctgg gcgcggcctcc gccccggcaa cgccgacttc accgacactg    1140
actggcttga caccgccttc ctcttctacg acgaggaggc ccgccccgtg cgcgtccgcg     1200
tccgcgactg cctcgacccg gccgccatgg gtacgcgta ccaggacgtc ggcctgccgt      1260
ggctgaaagc caagccggcc aagagatccc gcaggacgcc ggcgcccgcc gcgggcgcgc     1320
tcccggcgac gctgagggag accgtgcggg tgacggtgac aaggcccag gtgtcgagga      1380 gcgacaagga gaaggaggag gcggaggagg tgctgatcgt cgagggatc caggtcgccg      1440 accacttcaa gttcgtcaag ttcgacgtgc tggtgaacgc gcccgagagc ggaggcgatg     1500
ccgcgtcggg gtactgcgcc ggcagcgtcg cgatgacgcc gcacatggtc cggacgaaca     1560
agaagaaggg ctccgtgaag acggtggcga ggttcggcgc ctgcgacctg atggacaaca     1620
tcggggcaga cggcgacaag acggtggtcg tgtcgcttgt gcccaggtgc ggcggcgagc     1680
tggtcaccat cggcggcgtc agcatcggct ataccaagtg aagcaccgcc accgtatata     1740
ccgtgtggtg tatatctaaa caagtcgctc atgagcgatc gttgcgtgct ttacgtcacg     1800
tatgtctagc gtatattgcg ccgtatgtta cgtgcatcta ctgtgcttat attgcagcgt     1860
atgtctagcg tattctaata agaacaattg gaacggtgca ctttattgtc cttacttcat     1920
atatagtact catgttacaa gtacattaaa aaaaaaaaaa aaaaaaaaaa aaaaaaaaaa     1980
aaaaaaaaaa aaa                                                        1993
```

<210> SEQ ID NO 14
<211> LENGTH: 557
<212> TYPE: PRT
<213> ORGANISM: Triticum aestivum

<400> SEQUENCE: 14

```
Met Glu Ile Ser Thr Ser Val Ala Arg Cys Thr Arg Met Pro Cys Ser
  1               5                  10                  15

Leu Gln Ala Leu Val Pro Thr Lys Ala Arg Gln Thr Arg Arg Leu Thr
                 20                  25                  30

Cys Lys Ala Thr Gly Gly Arg Val Asp Arg Arg Asp Val Leu Leu Gly
             35                  40                  45

Leu Gly Ser Ala Ala Ala Gly Leu Gly Ala Gln Arg Ala Arg Gly
         50                  55                  60

Ala Ile Ala Ala Pro Ile Gln Ala Pro Asp Leu Gly Asn Cys Asn Pro
 65                  70                  75                  80

Pro Asp Leu Pro Asn Thr Ala Pro Asp Thr Asn Cys Cys Pro Thr Ser
                 85                  90                  95

Gly Thr Gly Ile Ile Asp Phe Val Leu Pro Pro Ala Ser Ser Ala Pro
            100                 105                 110

Leu Arg Val Arg Pro Ala Ala His Leu Ala Asp Ala Glu Tyr Leu Ala
        115                 120                 125

Lys Tyr Glu Arg Ala Val Ala Leu Met Lys Gln Leu Pro Ala Asp Asp
    130                 135                 140
```

-continued

```
Pro Arg Ser Phe Glu Gln Gln Trp Arg Val His Cys Ala Tyr Cys Asp
145                 150                 155                 160

Gly Ala Tyr Asp Gln Val Gly Phe Pro Asp Leu Glu Ile Gln Val His
            165                 170                 175

Asn Cys Trp Leu Phe Phe Pro Trp His Arg Phe Tyr Leu Tyr Phe His
        180                 185                 190

Glu Arg Ile Leu Gly Lys Leu Ile Gly Asp Asp Thr Phe Ala Leu Pro
    195                 200                 205

Phe Trp Asn Trp Asp Ala Pro Asp Gly Met Thr Leu Pro Ala Ile Tyr
210                 215                 220

Ala Asn Arg Ser Ser Pro Leu Tyr Asn Glu Arg Arg Asn Pro Ala His
225                 230                 235                 240

Gln Pro Pro Phe Pro Val Asp Leu Asp Phe Asn Glu Ile Asp Val Ile
            245                 250                 255

Ile Pro Thr Asp Glu Gln Ile Asp Gln Asn Leu Asn Ile Met Tyr Arg
        260                 265                 270

Gln Met Val Ser Gly Ala Lys Lys Thr Arg Leu Phe Met Gly Gln Pro
    275                 280                 285

Tyr Arg Ala Gly Asp Gln Pro Asp Pro Gly Ala Gly Ser Val Glu Asn
290                 295                 300

Val Pro His Gly Thr Met His Thr Trp Thr Gly Asp Pro Ala Gln Pro
305                 310                 315                 320

Asn Asn Glu Asp Met Gly Asn Phe Tyr Ser Ala Ala Arg Asp Pro Ile
            325                 330                 335

Phe Phe Ala His His Gly Asn Ile Asp Arg Leu Trp His Val Trp Arg
        340                 345                 350

Gly Leu Arg Pro Gly Asn Ala Asp Phe Thr Asp Thr Asp Trp Leu Asp
    355                 360                 365

Thr Ala Phe Leu Phe Tyr Asp Glu Glu Ala Arg Pro Val Arg Val Arg
370                 375                 380

Val Arg Asp Cys Leu Asp Pro Ala Ala Met Gly Tyr Ala Tyr Gln Asp
385                 390                 395                 400

Val Gly Leu Pro Trp Leu Lys Ala Lys Pro Ala Lys Arg Ser Arg Arg
            405                 410                 415

Thr Pro Ala Pro Ala Ala Gly Ala Leu Pro Ala Thr Leu Arg Glu Thr
        420                 425                 430

Val Arg Val Thr Val Thr Arg Pro Gln Val Ser Arg Ser Asp Lys Glu
    435                 440                 445

Lys Glu Glu Ala Glu Glu Val Leu Ile Val Glu Gly Ile Gln Val Ala
450                 455                 460

Asp His Phe Lys Phe Val Lys Phe Asp Val Leu Val Asn Ala Pro Glu
465                 470                 475                 480

Ser Gly Gly Asp Ala Ala Ser Gly Tyr Cys Ala Gly Ser Val Ala Met
            485                 490                 495

Thr Pro His Met Val Arg Thr Asn Lys Lys Gly Ser Val Lys Thr
        500                 505                 510

Val Ala Arg Phe Gly Val Cys Asp Leu Met Asp Asn Ile Gly Ala Asp
    515                 520                 525

Gly Asp Lys Thr Val Val Ser Leu Val Pro Arg Cys Gly Gly Glu
530                 535                 540

Leu Val Thr Ile Gly Gly Val Ser Ile Gly Tyr Thr Lys
545                 550                 555
```

<210> SEQ ID NO 15
<211> LENGTH: 852
<212> TYPE: DNA
<213> ORGANISM: Glycine max
<220> FEATURE:
<221> NAME/KEY: unsure
<222> LOCATION: (390)
<223> OTHER INFORMATION: n = a, c, g or t
<220> FEATURE:
<221> NAME/KEY: unsure
<222> LOCATION: (515)
<223> OTHER INFORMATION: n = a, c, g or t
<220> FEATURE:
<221> NAME/KEY: unsure
<222> LOCATION: (543)
<223> OTHER INFORMATION: n = a, c, g or t
<220> FEATURE:
<221> NAME/KEY: unsure
<222> LOCATION: (668)
<223> OTHER INFORMATION: n = a, c, g or t
<220> FEATURE:
<221> NAME/KEY: unsure
<222> LOCATION: (718)
<223> OTHER INFORMATION: n = a, c, g or t
<220> FEATURE:
<221> NAME/KEY: unsure
<222> LOCATION: (720)
<223> OTHER INFORMATION: n = a, c, g or t
<220> FEATURE:
<221> NAME/KEY: unsure
<222> LOCATION: (722)
<223> OTHER INFORMATION: n = a, c, g or t
<220> FEATURE:
<221> NAME/KEY: unsure
<222> LOCATION: (737)
<223> OTHER INFORMATION: n = a, c, g or t
<220> FEATURE:
<221> NAME/KEY: unsure
<222> LOCATION: (746)
<223> OTHER INFORMATION: n = a, c, g or t
<220> FEATURE:
<221> NAME/KEY: unsure
<222> LOCATION: (791)
<223> OTHER INFORMATION: n = a, c, g or t
<220> FEATURE:
<221> NAME/KEY: unsure
<222> LOCATION: (799)
<223> OTHER INFORMATION: n = a, c, g or t
<220> FEATURE:
<221> NAME/KEY: unsure
<222> LOCATION: (823)
<223> OTHER INFORMATION: n = a, c, g or t
<220> FEATURE:
<221> NAME/KEY: unsure
<222> LOCATION: (841)
<223> OTHER INFORMATION: n = a, c, g or t
<220> FEATURE:
<221> NAME/KEY: unsure
<222> LOCATION: (848)
<223> OTHER INFORMATION: n = a, c, g or t

<400> SEQUENCE: 15

| | | | | | |
|---|---|---|---|---|---|
| cccctctgat | gacccgcgta | atttcaccca | acaagccaac | gttcattgtg | cttattgtga | 60 |
| tggtgcatat | caccaagttg | ggttccctga | cctcgatctc | caagtccaca | actcctggct | 120 |
| cttcttccct | ttccatcgtt | ggtatcttta | tttctatgaa | aggatcttgg | ggagcttgat | 180 |
| caatgatcca | acctttgccc | ttccattttg | gaactgggat | gctcctaagg | gcatgcaact | 240 |
| tccttccatt | tacgcagacc | ctaaatcacc | cctttatgac | actctccgca | atgccaatca | 300 |
| tcaaccccca | acactcgtag | acctcgactt | caatctcgag | gatcctattt | ccaatggcaa | 360 |
| aatttccaac | aacctcacca | taatgtatan | gcaagttgtg | tctaacggga | agactcctac | 420 |
| attgttcctt | ggaaatcctt | accgtgctgg | ggatgagcct | gacccgggtt | ttggatcagt | 480 |

```
agagaatgtt ccacatggcc ctgttcatct ttggnccggt gatatcaacc aacctaacat      540
tgngaacatg ggaactttct attcagctgc aggagacccc atttttttatt ctcatcattc     600 agacattgat aagatgtggt ccatatggaa aacactttgt gggaaaagaa gggattttac     660
tgattcantt gggtaaaatc tgcgttctct tctacgatga taacaagaac cttgtgcntn     720
tnaaggcaag gatctcntga cactanaaac taggtatgtt tacaagattt gacatccatg     780
gttaattcta ccacccgnt tagtcagggt aaaaggacat tanacaaatt tgtgtgggga      840
ncatcgcnaa ct                                                         852
```

<210> SEQ ID NO 16
<211> LENGTH: 221
<212> TYPE: PRT
<213> ORGANISM: Glycine max
<220> FEATURE:
<221> NAME/KEY: UNSURE
<222> LOCATION: (130)
<223> OTHER INFORMATION: Xaa = any amino acid
<220> FEATURE:
<221> NAME/KEY: UNSURE
<222> LOCATION: (172)
<223> OTHER INFORMATION: Xaa = any amino acid
<220> FEATURE:
<221> NAME/KEY: UNSURE
<222> LOCATION: (181)
<223> OTHER INFORMATION: Xaa = any amino acid

<400> SEQUENCE: 16

```
Pro Ser Asp Asp Pro Arg Asn Phe Thr Gln Gln Ala Asn Val His Cys
  1               5                  10                  15
Ala Tyr Cys Asp Gly Ala Tyr His Gln Val Gly Phe Pro Asp Leu Asp
             20                  25                  30
Leu Gln Val His Asn Ser Trp Leu Phe Phe Pro Phe His Arg Trp Tyr
         35                  40                  45
Leu Tyr Phe Tyr Glu Arg Ile Leu Gly Ser Leu Ile Asn Asp Pro Thr
     50                  55                  60
Phe Ala Leu Pro Phe Trp Asn Trp Asp Ala Pro Lys Gly Met Gln Leu
 65                  70                  75                  80
Pro Ser Ile Tyr Ala Asp Pro Lys Ser Pro Leu Tyr Asp Thr Leu Arg
                 85                  90                  95
Asn Ala Asn His Gln Pro Pro Thr Leu Val Asp Leu Asp Phe Asn Leu
            100                 105                 110
Glu Asp Pro Ile Ser Asn Gly Lys Ile Ser Asn Asn Leu Thr Ile Met
        115                 120                 125
Tyr Xaa Gln Val Val Ser Asn Gly Lys Thr Pro Thr Leu Phe Leu Gly
    130                 135                 140
Asn Pro Tyr Arg Ala Gly Asp Glu Pro Asp Pro Gly Phe Gly Ser Val
145                 150                 155                 160
Glu Asn Val Pro His Gly Pro Val His Leu Trp Xaa Gly Asp Ile Asn
                165                 170                 175
Gln Pro Asn Ile Xaa Asn Met Gly Thr Phe Tyr Ser Ala Ala Gly Asp
            180                 185                 190
Pro Ile Phe Tyr Ser His His Ser Asp Ile Asp Lys Met Trp Ser Ile
        195                 200                 205
Trp Lys Thr Leu Cys Gly Lys Arg Arg Asp Phe Thr Asp
    210                 215                 220
```

<210> SEQ ID NO 17

<211> LENGTH: 522
<212> TYPE: DNA
<213> ORGANISM: Glycine max

<400> SEQUENCE: 17

```
atctctcctc tatccttcgt gcccacagtc aataatgtct cttccaactc catcgctccc      60
ccttctccgt tgcatccatt ttcacgattc caatccatta aaaatagaaa gccaaaaccc     120
catcatattc ctagaatcac atgcagtgga aaccaaaaca atccaacacc aaaccctaat     180
tcccagggag aacctccaca tattgtagga cataggagga acgttctact tggcctagga     240
gggctttgtg gtgctgttac tcttaacaac aacaacccct ttgcctttgc agctccaata     300
tctcctcctg acctaaacac gtgcggtcca ccagacctac ccgcaggtgt aaacccacc      360
aattgttgcc ccccatcttc caaaatcata gatttcaagt tctctccctc taaccaaccc     420
ttgagggtaa gaccagccgc acatttggtc aacgatgagt atctagccaa atacaaaaaa     480
agccttgacc tcatgaaaaa actcccctct gatgaccggg tt                       522
```

<210> SEQ ID NO 18
<211> LENGTH: 174
<212> TYPE: PRT
<213> ORGANISM: Glycine max

<400> SEQUENCE: 18

```
Ile Ser Pro Leu Ser Phe Val Pro Thr Val Asn Asn Val Ser Ser Asn
 1               5                  10                  15

Ser Ile Ala Pro Pro Ser Pro Leu His Pro Phe Ser Arg Phe Gln Ser
            20                  25                  30

Ile Lys Asn Arg Lys Pro Lys Pro His His Ile Pro Arg Ile Thr Cys
        35                  40                  45

Ser Gly Asn Gln Asn Asn Pro Thr Pro Asn Pro Asn Ser Gln Gly Glu
    50                  55                  60

Pro Pro His Ile Val Gly His Arg Arg Asn Val Leu Leu Gly Leu Gly
65                  70                  75                  80

Gly Leu Cys Gly Ala Val Thr Leu Asn Asn Asn Asn Pro Phe Ala Phe
                85                  90                  95

Ala Ala Pro Ile Ser Pro Pro Asp Leu Asn Thr Cys Gly Pro Pro Asp
            100                 105                 110

Leu Pro Ala Gly Val Lys Pro Thr Asn Cys Cys Pro Pro Ser Ser Lys
        115                 120                 125

Ile Ile Asp Phe Lys Phe Ser Pro Ser Asn Gln Pro Leu Arg Val Arg
    130                 135                 140

Pro Ala Ala His Leu Val Asn Asp Glu Tyr Leu Ala Lys Tyr Lys Lys
145                 150                 155                 160

Ser Leu Asp Leu Met Lys Lys Leu Pro Ser Asp Asp Arg Val
                165                 170
```

<210> SEQ ID NO 19
<211> LENGTH: 1989
<212> TYPE: DNA
<213> ORGANISM: Glycine max

<400> SEQUENCE: 19

```
gcacgagatc tctcctctat ccttcgtgcc cacagtcaat aatgtctctt ccaactccat      60
cgctccccct tctccgttgc atccattttc acgattccaa tccattaaaa atagaaagcc     120
aaaaccccat catattccta gaatcacatg cagtggaaac caaacaatc caacaccaaa     180
```

-continued

```
ccctaattcc caggagaac ctccacatat tgtaggacat aggaggaacg ttctacttgg    240
cctaggaggg ctttgtggtg ctgttactct taacaacaac aaccctttg cctttgcagc    300 tccaatatct cctcctgacc taaacacgtg cggtccacca gacctacccg caggtgtaaa    360
acccaccaat tgttgccccc catcttccaa aatcatagat ttcaagttct ctccctctaa    420
ccaacccttg agggtaagac cagccgcaca tttggtcaac gatgagtatc tagccaaata    480
caaaaaagcc cttgacctca tgaaaaaact cccctctgat gacccgcgta atttcaccca    540
acaagccaac gttcattgtg cttattgtga tggtgcatat caccaagttg ggttccctga    600
cctcgatctc caagtccaca actcctggct cttcttccct ttccatcgtt ggtatcttta    660
tttctatgaa aggatcttgg ggagcttgat caatgatcca acctttgccc ttccattttg    720
gaactgggat gctcctaagg gcatgcaact tccttccatt tacgcagacc ctaaatcacc    780
cctttatgac actctccgca atgccaatca tcaaccccca acactcgtag acctcgactt    840
caatctcgag gatcctattt ccaatggcaa aatttccaac aacctcacca taatgtatag    900
gcaagttgtg tctaacggga agactcctac attgttcctt ggaaatcctt accgtgctgg    960
ggatgagcct gacccgggtt ttggatcagt agagaatgtt ccacatggcc ctgttcatct    1020
ttggaccggt gatatcaacc aacctaacat tgagaacatg ggaactttct attcagctgc    1080
aagagacccc atttttttatt ctcatcattc aaacattgat aggatgtggt ccatatggaa    1140
aacacttggt gggaaaagaa gggattttac tgattcagat tggttagaat ctgcgtttct    1200
cttctacgat gagaacaaga accttgtgcg tgtgaaggtc aaggattctc ttgacactag    1260
aaaactaggg tatgtttacc aagatgttga cattccatgg ttaaattcta agcccacgcc    1320
gcgtaggtca aggttcaga aggtagcatt agcacaaaat tttggtgttg gtgcagcaca    1380
tgctgctgag acttcaagga atgtgaagtt cccactagtg ttggattcag ttgtgagcac    1440
aatggttaaa aggccaaaca agtcgaggag caagaaggaa aaggaagagg aggaagaggt    1500
tttggtgatt gaagggattg agtttgagag aaacacacct gtgaaatttg atgtgtttat    1560
caatgatgaa gatgataagc agattcgacc agataataca gaatttgcag gaagctttgt    1620
gagtgtgcct cattcacata tgcacaaaaa caaggacatc attacttgtt tgaggctggg    1680
acttacggat ttgttggaag aattggaagc ggaagatgat gacagtgtta gggtgacgct    1740
ggttccgaga tatgggaaag ggcgtgttaa aatcagaggc atcaaaatag agcttctttc    1800
ggattgaaaa ttatctatat gcttcaacta cttatatatg tgtgtgtggt aatacatata    1860
tggttactag tttccaataa agtgtgtaac tcataaagag atattatgta tttcctatca    1920
tatgctgatt catttaatac ttgataaata aataaaaga ttaatgcgta aaaaaaaaa    1980 aaaaaaaa                                                            1989
```

<210> SEQ ID NO 20
<211> LENGTH: 599
<212> TYPE: PRT
<213> ORGANISM: Glycine max

<400> SEQUENCE: 20

```
Ile Ser Pro Leu Ser Phe Val Pro Thr Val Asn Asn Val Ser Asn
 1               5                  10                  15

Ser Ile Ala Pro Pro Ser Pro Leu His Pro Phe Ser Arg Phe Gln Ser
            20                  25                  30

Ile Lys Asn Arg Lys Pro Lys Pro His His Ile Pro Arg Ile Thr Cys
        35                  40                  45
```

```
Ser Gly Asn Gln Asn Asn Pro Thr Pro Asn Pro Asn Ser Gln Gly Glu
    50                  55                  60

Pro Pro His Ile Val Gly His Arg Arg Asn Val Leu Gly Leu Gly
65              70                  75                  80

Gly Leu Cys Gly Ala Val Thr Leu Asn Asn Asn Asn Pro Phe Ala Phe
            85                  90                  95

Ala Ala Pro Ile Ser Pro Pro Asp Leu Asn Thr Cys Gly Pro Pro Asp
            100                 105                 110

Leu Pro Ala Gly Val Lys Pro Thr Asn Cys Cys Pro Pro Ser Ser Lys
            115                 120                 125

Ile Ile Asp Phe Lys Phe Ser Pro Ser Asn Gln Pro Leu Arg Val Arg
            130                 135                 140

Pro Ala Ala His Leu Val Asn Asp Glu Tyr Leu Ala Lys Tyr Lys Lys
145                 150                 155                 160

Ala Leu Asp Leu Met Lys Lys Leu Pro Ser Asp Asp Pro Arg Asn Phe
                165                 170                 175

Thr Gln Gln Ala Asn Val His Cys Ala Tyr Cys Asp Gly Ala Tyr His
            180                 185                 190

Gln Val Gly Phe Pro Asp Leu Asp Leu Gln Val His Asn Ser Trp Leu
        195                 200                 205

Phe Phe Pro Phe His Arg Trp Tyr Leu Tyr Phe Tyr Glu Arg Ile Leu
    210                 215                 220

Gly Ser Leu Ile Asn Asp Pro Thr Phe Ala Leu Pro Phe Trp Asn Trp
225                 230                 235                 240

Asp Ala Pro Lys Gly Met Gln Leu Pro Ser Ile Tyr Ala Asp Pro Lys
            245                 250                 255

Ser Pro Leu Tyr Asp Thr Leu Arg Asn Ala Asn His Gln Pro Pro Thr
            260                 265                 270

Leu Val Asp Leu Asp Phe Asn Leu Glu Asp Pro Ile Ser Asn Gly Lys
            275                 280                 285

Ile Ser Asn Asn Leu Thr Ile Met Tyr Arg Gln Val Val Ser Asn Gly
            290                 295                 300

Lys Thr Pro Thr Leu Phe Leu Gly Asn Pro Tyr Arg Ala Gly Asp Glu
305                 310                 315                 320

Pro Asp Pro Gly Phe Gly Ser Val Glu Asn Val Pro His Gly Pro Val
            325                 330                 335

His Leu Trp Thr Gly Asp Ile Asn Gln Pro Asn Ile Glu Asn Met Gly
            340                 345                 350

Thr Phe Tyr Ser Ala Ala Arg Asp Pro Ile Phe Tyr Ser His His Ser
            355                 360                 365

Asn Ile Asp Arg Met Trp Ser Ile Trp Lys Thr Leu Gly Gly Lys Arg
            370                 375                 380

Arg Asp Phe Thr Asp Ser Asp Trp Leu Glu Ser Ala Phe Leu Phe Tyr
385                 390                 395                 400

Asp Glu Asn Lys Asn Leu Val Arg Val Lys Val Lys Asp Ser Leu Asp
            405                 410                 415

Thr Arg Lys Leu Gly Tyr Val Tyr Gln Asp Val Asp Ile Pro Trp Leu
            420                 425                 430

Asn Ser Lys Pro Thr Pro Arg Arg Ser Arg Val Gln Lys Val Ala Leu
            435                 440                 445

Ala Gln Asn Phe Gly Val Gly Ala Ala His Ala Glu Thr Ser Arg
            450                 455                 460

Asn Val Lys Phe Pro Leu Val Leu Asp Ser Val Val Ser Thr Met Val
```

```
          465                 470                 475                 480
Lys Arg Pro Asn Lys Ser Arg Ser Lys Lys Glu Lys Glu Glu Glu Glu
                        485                 490                 495

Glu Val Leu Val Ile Glu Gly Ile Glu Phe Glu Arg Asn Thr Pro Val
                500                 505                 510

Lys Phe Asp Val Phe Ile Asn Asp Glu Asp Lys Gln Ile Arg Pro
            515                 520                 525

Asp Asn Thr Glu Phe Ala Gly Ser Phe Val Ser Val Pro His Ser His
        530                 535                 540

Met His Lys Asn Lys Asp Ile Ile Thr Cys Leu Arg Leu Gly Leu Thr
545                 550                 555                 560

Asp Leu Leu Glu Glu Leu Glu Ala Glu Asp Asp Asp Ser Val Arg Val
                565                 570                 575

Thr Leu Val Pro Arg Tyr Gly Lys Gly Arg Val Lys Ile Arg Gly Ile
            580                 585                 590

Lys Ile Glu Leu Leu Ser Asp
        595
```

```
<210> SEQ ID NO 21
<211> LENGTH: 887
<212> TYPE: DNA
<213> ORGANISM: Glycine max
<220> FEATURE:
<221> NAME/KEY: unsure
<222> LOCATION: (33)
<223> OTHER INFORMATION: n = a, c, g or t
<220> FEATURE:
<221> NAME/KEY: unsure
<222> LOCATION: (60)
<223> OTHER INFORMATION: n = a, c, g or t
<220> FEATURE:
<221> NAME/KEY: unsure
<222> LOCATION: (618)
<223> OTHER INFORMATION: n = a, c, g or t
<220> FEATURE:
<221> NAME/KEY: unsure
<222> LOCATION: (792)
<223> OTHER INFORMATION: n = a, c, g or t
<220> FEATURE:
<221> NAME/KEY: unsure
<222> LOCATION: (854)
<223> OTHER INFORMATION: n = a, c, g or t
<220> FEATURE:
<221> NAME/KEY: unsure
<222> LOCATION: (865)
<223> OTHER INFORMATION: n = a, c, g or t

<400> SEQUENCE: 21
cgacccgatt ttttttctc acccattcta acnttgttag gatgtggtcc catatgaaan      60
cgcttgttgg aaaaggaaag gattttactg actcggattg gttagaatct gggtttctct   120
tctacgatga gaataagaac cttgtgcgag taaaggttaa agattgtctt gacgagagaa   180
aactagggta tgtttaccaa gatgtagaca ttccatggtt aaactctagg cccacaccgc   240
gaaggtctag ggttcaaaag gttgcactag cacaaaattt tggtgttggt gcagcacgtg   300
ctgctgagac ttcaaggaat gtgaagttcc cactagtgtt ggattcagtt gtgagcacaa   360
tggttaaaag gccaaacaag tcgaggagca agaaggagaa ggaagaggag gaagaggttt   420
tggtgattga agggattgag tttgagagaa acacacctgt gaaatttgat gtgtttatca   480
atgatgaaga tgataagcag attcgaccag ataatacaga atttgcagga agctttgtga   540
gtgtgcctca ttcacatatg cacaaaaaca aggacatcat tacttgtttg aggctgggac   600
ttacggattt gttggaanga attggaagcg aagatgatg acagtgttag ggtgacgctg   660
```

-continued

```
gttccgagat atgggaaagg gcgtgttaaa atcaagaggc atcaaaatag agcttctttc      720
ggattgaaaa ttatctatat gcttcaacta cttatatatg tgtgtgtggt aatacatata      780
tggttactaa gnttccaata aagtgtgtaa ctcataaaga gatattatgt atttcctatc      840
atatgctgat tcanttaata ctganaaata actaaaagat tatgctt                    887
```

<210> SEQ ID NO 22
<211> LENGTH: 265
<212> TYPE: PRT
<213> ORGANISM: Glycine max
<220> FEATURE:
<221> NAME/KEY: UNSURE
<222> LOCATION: (11)
<223> OTHER INFORMATION: Xaa = any amino acid
<220> FEATURE:
<221> NAME/KEY: UNSURE
<222> LOCATION: (20)
<223> OTHER INFORMATION: Xaa = any amino acid
<220> FEATURE:
<221> NAME/KEY: UNSURE
<222> LOCATION: (263)
<223> OTHER INFORMATION: Xaa = any amino acid

<400> SEQUENCE: 22

Asp Pro Ile Phe Phe Ser His His Ser Asn Xaa Val Arg Met Trp Ser
 1               5                  10                  15

His Met Lys Xaa Leu Val Gly Lys Gly Lys Asp Phe Thr Asp Ser Asp
             20                  25                  30

Trp Leu Glu Ser Gly Phe Leu Phe Tyr Asp Glu Asn Lys Asn Leu Val
         35                  40                  45

Arg Val Lys Val Lys Asp Cys Leu Asp Glu Arg Lys Leu Gly Tyr Val
     50                  55                  60

Tyr Gln Asp Val Asp Ile Pro Trp Leu Asn Ser Arg Pro Thr Pro Arg
 65                  70                  75                  80

Arg Ser Arg Val Gln Lys Val Ala Leu Ala Gln Asn Phe Gly Val Gly
                 85                  90                  95

Ala Ala Arg Ala Ala Glu Thr Ser Arg Asn Val Lys Phe Pro Leu Val
            100                 105                 110

Leu Asp Ser Val Val Ser Thr Met Val Lys Arg Pro Asn Lys Ser Arg
        115                 120                 125

Ser Lys Lys Glu Lys Glu Glu Glu Glu Val Leu Val Ile Glu Gly
    130                 135                 140

Ile Glu Phe Glu Arg Asn Thr Pro Val Lys Phe Asp Val Phe Ile Asn
145                 150                 155                 160

Asp Glu Asp Asp Lys Gln Ile Arg Pro Asp Asn Thr Glu Phe Ala Gly
                165                 170                 175

Ser Phe Val Ser Val Pro His Ser His Met His Lys Asn Lys Asp Ile
            180                 185                 190

Ile Thr Cys Leu Arg Leu Gly Leu Thr Asp Leu Leu Glu Glu Leu Glu
        195                 200                 205

Ala Glu Asp Asp Asp Ser Val Arg Val Thr Leu Val Pro Arg Tyr Gly
    210                 215                 220

Lys Gly Arg Val Lys Ile Lys Arg His Gln Asn Arg Ala Ser Phe Gly
225                 230                 235                 240

Leu Lys Ile Ile Tyr Met Leu Gln Leu Leu Ile Tyr Val Cys Val Val
                245                 250                 255

Ile His Ile Trp Leu Leu Xaa Phe Gln
            260                 265

<210> SEQ ID NO 23
<211> LENGTH: 510
<212> TYPE: DNA
<213> ORGANISM: Glycine max
<220> FEATURE:
<221> NAME/KEY: unsure
<222> LOCATION: (478)
<223> OTHER INFORMATION: n = a, c, g or t

<400> SEQUENCE: 23

```
gtccttttc cttcgtgtcc gtagtcaata atgcctcttc caactcctcc accactcccc      60
cttcttcctt gcatccaatt tcacaattcc aatccactaa aaatagaaag ccaaaacgcc    120
atcacattcc tagaaccaca tgcagtgaaa accaaaacaa tccaacacca aacccatccg    180
aaggagaact atcacatatt gtaggacata ggaggaatgt tctacttggc ctaggagggc    240
tttgtggtgc agttactctt aacaacaacc cttttgcctt tgcagctcca atatctcctc    300
cagacctaaa cacacatgtg gtccaccaga cacaccgcg ggtgcaaatc ccaccaattt     360
gttgccccc atcttccaaa aatcatagat ttcaaggtt ccctccttct aaaccaaccc     420
cttgagggta agaccaagcg ggcacatttg ggtcaaaccg atgaaataat ctaagccnaa    480
aatacaaaaa aaggcccttt gacctcaatg                                    510
```

<210> SEQ ID NO 24
<211> LENGTH: 138
<212> TYPE: PRT
<213> ORGANISM: Glycine max

<400> SEQUENCE: 24

```
Pro Phe Ser Phe Val Ser Val Val Asn Asn Ala Ser Ser Asn Ser Ser
 1               5                  10                  15

Thr Thr Pro Pro Ser Ser Leu His Pro Ile Ser Gln Phe Gln Ser Thr
            20                  25                  30

Lys Asn Arg Lys Pro Lys Arg His His Ile Pro Arg Thr Thr Cys Ser
        35                  40                  45

Glu Asn Gln Asn Asn Pro Thr Pro Asn Pro Ser Glu Gly Glu Leu Ser
    50                  55                  60

His Ile Val Gly His Arg Arg Asn Val Leu Leu Gly Leu Gly Gly Leu
65                  70                  75                  80

Cys Gly Ala Val Thr Leu Asn Asn Asn Pro Phe Ala Phe Ala Ala Pro
                85                  90                  95

Ile Ser Pro Pro Asp Leu Asn Thr His Val Val His Gln Thr His Pro
            100                 105                 110

Arg Val Gln Ile Pro Pro Ile Cys Cys Pro Pro Ser Ser Lys Asn His
        115                 120                 125

Arg Phe Gln Arg Phe Pro Pro Ser Lys Pro
    130                 135
```

<210> SEQ ID NO 25
<211> LENGTH: 988
<212> TYPE: DNA
<213> ORGANISM: Glycine max
<220> FEATURE:
<221> NAME/KEY: unsure
<222> LOCATION: (962)
<223> OTHER INFORMATION: n = a, c, g or t
<220> FEATURE:
<221> NAME/KEY: unsure
<222> LOCATION: (970)..(971)
<223> OTHER INFORMATION: n = a, c, g or t

<400> SEQUENCE: 25

```
ctctcctata tccttcgtga gtgcaatcaa taatgtctct tccaactcat ccaattcccc      60
ttcttccttg catcatccct tttcacaaat tcaatccgct aaatatcgaa aaccaaaacg     120
ccatcatcat attcctagag tgacatgcag tgacaaccaa aaaccaaaca catctggaga     180
actagtactc ccacatagga ggaacattct acttggccta ggagggcttt gtggtgctgc     240
tgctactctt aacaacatcc cttttgccaa tgctgcccca atacttggtc cagacctaac     300
cacatgtgtt caagcagaac tacccgaagg tgtagaaccc accaattgtt gtcccccaat     360
ttccacaaac atcatagatt tcaagttccc tccctccaac caacccttgc gtgtacgatc     420
cgctgctcat ctggtcaaca aagactatct agctaaatac gagaaagccg ttaacctgat     480
gaaaaatctc ccgtcagatg atccacgtag tttcgcgcaa caagccaaag ttcattgtgc     540
ttattgcgac ggtggatatc accaactagg cttccctgac cttgatctcg aagtgcactt     600
ctcttggctc ttctttcctt accacagatg gtatctctat ttccatgaaa ggatattggc     660
gagcttgatc aatgatccaa cctttgctct tccattttgg aactgggatg ctcctggggg     720
catgcaactt ccttccatgt acgcagatcc caaatcaccc ctttatgatt ctctacgcaa     780
tgccaaccat caaccaccaa cacttgtaaa ccttgacttt actatcgagg atcctaatgc     840
agaggcaaat atctccacca acctcaccac aatgtatagg caagcttgtg tctaacgcaa     900
agactccaac attgttcttc ggaaatcctt atcgtgctgg ggatcagcta accctggtgg     960
gnggtccgtn nagagcactc cacatggg                                        988
```

<210> SEQ ID NO 26
<211> LENGTH: 274
<212> TYPE: PRT
<213> ORGANISM: Glycine max

<400> SEQUENCE: 26

```
Ser Pro Ile Ser Phe Val Ser Ala Ile Asn Asn Val Ser Ser Asn Ser
  1               5                  10                  15
Ser Asn Ser Pro Ser Ser Leu His His Pro Phe Ser Gln Ile Gln Ser
             20                  25                  30
Ala Lys Tyr Arg Lys Pro Lys Arg His His Ile Pro Arg Val Thr
         35                  40                  45
Cys Ser Asp Asn Gln Lys Pro Asn Thr Ser Gly Glu Leu Val Leu Pro
     50                  55                  60
His Arg Arg Asn Ile Leu Leu Gly Leu Gly Gly Leu Cys Gly Ala Ala
 65                  70                  75                  80
Ala Thr Leu Asn Asn Ile Pro Phe Ala Asn Ala Ala Pro Ile Leu Gly
                 85                  90                  95
Pro Asp Leu Thr Thr Cys Val Gln Ala Glu Leu Pro Glu Gly Val Glu
            100                 105                 110
Pro Thr Asn Cys Cys Pro Pro Ile Ser Thr Asn Ile Ile Asp Phe Lys
        115                 120                 125
Phe Pro Pro Ser Asn Gln Pro Leu Arg Val Arg Ser Ala Ala His Leu
    130                 135                 140
Val Asn Lys Asp Tyr Leu Ala Lys Tyr Glu Lys Ala Val Asn Leu Met
145                 150                 155                 160
Lys Asn Leu Pro Ser Asp Asp Pro Arg Ser Phe Ala Gln Gln Ala Lys
                165                 170                 175
Val His Cys Ala Tyr Cys Asp Gly Gly Tyr His Gln Leu Gly Phe Pro
```

-continued

```
                180             185             190
Asp Leu Asp Leu Glu Val His Phe Ser Trp Leu Phe Pro Tyr His
            195                 200             205
Arg Trp Tyr Leu Tyr Phe His Glu Arg Ile Leu Ala Ser Leu Ile Asn
        210                 215                 220
Asp Pro Thr Phe Ala Leu Pro Phe Trp Asn Trp Asp Ala Pro Gly Gly
225                 230                 235                 240
Met Gln Leu Pro Ser Met Tyr Ala Asp Pro Lys Ser Pro Leu Tyr Asp
                245                 250                 255
Ser Leu Arg Asn Ala Asn His Gln Pro Pro Thr Leu Val Asn Leu Asp
            260                 265                 270
Phe Thr
```

<210> SEQ ID NO 27
<211> LENGTH: 2044
<212> TYPE: DNA
<213> ORGANISM: Glycine max

<400> SEQUENCE: 27

```
gcacgagctc tcctatatcc ttcgtgagtg caatcaataa tgtctcttcc aactcatcca     60
attccccttc ttccttgcat catccctttt cacaaattca atccgctaaa tatcgaaaac    120
caaaacgcca tcatcatatt cctagagtga catgcagtga caaccaaaaa ccaaacacat    180
ctggagaact agtactccca cataggagga acattctact tggcctagga gggctttgtg    240
gtgctgctgc tactcttaac aacatccctt ttgccaatgc tgccccaata cttggtccag    300
acctaaccac atgtgttcaa gcagaactac ccgaaggtgt agaacccacc aattgttgtc    360
ccccaatttc cacaaacatc atagatttca gttccctcc ctccaaccaa cccttgcgtg    420
tacgatccgc tgctcatctg gtcaacaaag actatctagc taaatacgag aaagccgtta    480
acctgatgaa aaatctcccg tcagatgatc cacgtagttt cgcgcaacaa gccaaagttc    540
attgtgctta ttgcgacggt ggatatcacc aactaggctt ccctgacctt gatctcgaag    600
tgcacttctc ttggctcttc tttccttacc acagatggta tctctatttc catgaaagga    660
tattggcgag cttgatcaat gatccaacct ttgctcttcc attttggaac tgggatgctc    720
ctgggggcat gcaacttcct tccatgtacg cagatcccaa atcacccctt tatgattctc    780
tacgcaatgc caaccatcaa ccaccaacac ttgtaaacct tgactttact atcgaggatc    840
ctaatgcaga ggcaaatatc tccaccaacc tcaccacaat gtataggcag cttgtgtcta    900
acgcaaagac tccaacattg ttcttcggaa atccttatcg tgctggggat cagcctaacc    960
ctggtggtgg ctccgtagag agcactccac atggtcctgt tcatgcatgg accggtgata   1020
tcaaccaccc tacaatggag gacatgggga atttatatgc agctgcaaga gaccccattt   1080
tctattgcca ccattccaat gttgatagga tgtggtccat atggaaaaca cttggtggga   1140
aagaaggga tttaacagac ccggattggt tagaatccgc gtttctcttc tacgatgaga   1200
ataagaacct tgtgcgtgtg aagactaagg attgtcttga cacgagaaag ttagggtatg   1260
tttaccaaga tgttgacatt ccatggttaa aatctaagcc tacgccatta aggtcaaggg   1320
ctcaaaaggt agaactgaca ccacttttttg gtggtgttgc tgcagcacat gctgctgaga   1380
cttcaaggaa tgtgaagttc ccattggtgt tggattcagt tgtgagtaca gtggtgaaga   1440
ggccaaagaa gtctagggagc aaaaaggaga aggaagagaa ggaggagatt ctggtggttg   1500
aagggattga gtttgagagc agcacaggtg tgaagtttga tgtgtttatt aatgatgaag   1560
```

-continued

```
atgataagtt ggtcaagcca gataatacgg agtttgcagg aagctttgtg agtgtgcctc    1620
attcgcatga gcatcacaaa acaacaaga agattgttac ttgtttgagg ttgggactaa    1680
cggatttgtt ggaagaattg ggagcagaag atgatgatag tgttctagta acattggttc    1740
ccaagtatgg gaaagggcga gttaacatca gaggcatcaa gatagatttt gtttcagatt    1800
gaaattaaat tgtttatata cttcaaatgt gtgtttgtgc tgtaggtagt aatgcacgca    1860
tggttccttg aagaatttca aatgacgcag gtcactcaga cggagatata tatagtgtat    1920
ttcctataat ataagtttga gacatgtatt agaataatat agcatatcct tattatccta    1980
tgttcactta ctgtgaaata aataatatt gttgtgatat aaaaaaaaaa aaaaaaaaa     2040 aaaa                                                                 2044
```

<210> SEQ ID NO 28
<211> LENGTH: 599
<212> TYPE: PRT
<213> ORGANISM: Glycine max

<400> SEQUENCE: 28

```
Thr Ser Ser Pro Ile Ser Phe Val Ser Ala Ile Asn Asn Val Ser Ser
  1               5                  10                  15

Asn Ser Ser Asn Ser Pro Ser Ser Leu His His Pro Phe Ser Gln Ile
             20                  25                  30

Gln Ser Ala Lys Tyr Arg Lys Pro Lys Arg His His Ile Pro Arg
         35                  40                  45

Val Thr Cys Ser Asp Asn Gln Lys Pro Asn Thr Ser Gly Glu Leu Val
     50                  55                  60

Leu Pro His Arg Arg Asn Ile Leu Leu Gly Leu Gly Gly Leu Cys Gly
 65                  70                  75                  80

Ala Ala Ala Thr Leu Asn Asn Ile Pro Phe Ala Asn Ala Pro Ile
                 85                  90                  95

Leu Gly Pro Asp Leu Thr Thr Cys Val Gln Ala Glu Leu Pro Glu Gly
            100                 105                 110

Val Glu Pro Thr Asn Cys Cys Pro Pro Ile Ser Thr Asn Ile Ile Asp
        115                 120                 125

Phe Lys Phe Pro Pro Ser Asn Gln Pro Leu Arg Val Arg Ser Ala Ala
    130                 135                 140

His Leu Val Asn Lys Asp Tyr Leu Ala Lys Tyr Glu Lys Ala Val Asn
145                 150                 155                 160

Leu Met Lys Asn Leu Pro Ser Asp Asp Pro Arg Ser Phe Ala Gln Gln
                165                 170                 175

Ala Lys Val His Cys Ala Tyr Cys Asp Gly Gly Tyr His Gln Leu Gly
            180                 185                 190

Phe Pro Asp Leu Asp Leu Glu Val His Phe Ser Trp Leu Phe Phe Pro
        195                 200                 205

Tyr His Arg Trp Tyr Leu Tyr Phe His Glu Arg Ile Leu Ala Ser Leu
    210                 215                 220

Ile Asn Asp Pro Thr Phe Ala Leu Pro Phe Trp Asn Trp Asp Ala Pro
225                 230                 235                 240

Gly Gly Met Gln Leu Pro Ser Met Tyr Ala Asp Pro Lys Ser Pro Leu
                245                 250                 255

Tyr Asp Ser Leu Arg Asn Ala Asn His Gln Pro Pro Thr Leu Val Asn
            260                 265                 270

Leu Asp Phe Thr Ile Glu Asp Pro Asn Ala Glu Ala Asn Ile Ser Thr
        275                 280                 285
```

```
Asn Leu Thr Thr Met Tyr Arg Gln Leu Val Ser Asn Ala Lys Thr Pro
    290                 295                 300

Thr Leu Phe Phe Gly Asn Pro Tyr Arg Ala Gly Asp Gln Pro Asn Pro
305                 310                 315                 320

Gly Gly Gly Ser Val Glu Ser Thr Pro His Gly Pro Val His Ala Trp
                325                 330                 335

Thr Gly Asp Ile Asn His Pro Thr Met Glu Asp Met Gly Asn Leu Tyr
                340                 345                 350

Ala Ala Ala Arg Asp Pro Ile Phe Tyr Cys His His Ser Asn Val Asp
            355                 360                 365

Arg Met Trp Ser Ile Trp Lys Thr Leu Gly Gly Lys Arg Arg Asp Leu
    370                 375                 380

Thr Asp Pro Asp Trp Leu Glu Ser Ala Phe Leu Phe Tyr Asp Glu Asn
385                 390                 395                 400

Lys Asn Leu Val Arg Val Lys Thr Lys Asp Cys Leu Asp Thr Arg Lys
                405                 410                 415

Leu Gly Tyr Val Tyr Gln Asp Val Asp Ile Pro Trp Leu Lys Ser Lys
            420                 425                 430

Pro Thr Pro Leu Arg Ser Arg Ala Gln Lys Val Glu Leu Thr Pro Leu
    435                 440                 445

Phe Gly Gly Val Ala Ala His Ala Ala Glu Thr Ser Arg Asn Val
    450                 455                 460

Lys Phe Pro Leu Val Leu Asp Ser Val Val Ser Thr Val Lys Arg
465                 470                 475                 480

Pro Lys Lys Ser Arg Ser Lys Lys Glu Lys Glu Lys Glu Ile
                485                 490                 495

Leu Val Val Glu Gly Ile Glu Phe Glu Ser Ser Thr Gly Val Lys Phe
            500                 505                 510

Asp Val Phe Ile Asn Asp Glu Asp Lys Leu Val Lys Pro Asp Asn
            515                 520                 525

Thr Glu Phe Ala Gly Ser Phe Val Ser Val Pro His Ser His Glu His
    530                 535                 540

His Lys Asn Asn Lys Lys Ile Val Thr Cys Leu Arg Leu Gly Leu Thr
545                 550                 555                 560

Asp Leu Leu Glu Glu Leu Gly Ala Glu Asp Asp Ser Val Leu Val
                565                 570                 575

Thr Leu Val Pro Lys Tyr Gly Lys Gly Arg Val Asn Ile Arg Gly Ile
            580                 585                 590

Lys Ile Asp Phe Val Ser Asp
        595

<210> SEQ ID NO 29
<211> LENGTH: 685
<212> TYPE: DNA
<213> ORGANISM: Glycine max
<220> FEATURE:
<221> NAME/KEY: unsure
<222> LOCATION: (478)
<223> OTHER INFORMATION: n = a, c, g or t
<220> FEATURE:
<221> NAME/KEY: unsure
<222> LOCATION: (480)
<223> OTHER INFORMATION: n = a, c, g or t
<220> FEATURE:
<221> NAME/KEY: unsure
<222> LOCATION: (555)
<223> OTHER INFORMATION: n = a, c, g or t
<220> FEATURE:
```

```
<221> NAME/KEY: unsure
<222> LOCATION: (570)
<223> OTHER INFORMATION: n = a, c, g or t
<220> FEATURE:
<221> NAME/KEY: unsure
<222> LOCATION: (588)
<223> OTHER INFORMATION: n = a, c, g or t
<220> FEATURE:
<221> NAME/KEY: unsure
<222> LOCATION: (590)
<223> OTHER INFORMATION: n = a, c, g or t
<220> FEATURE:
<221> NAME/KEY: unsure
<222> LOCATION: (607)
<223> OTHER INFORMATION: n = a, c, g or t
<220> FEATURE:
<221> NAME/KEY: unsure
<222> LOCATION: (613)
<223> OTHER INFORMATION: n = a, c, g or t
<220> FEATURE:
<221> NAME/KEY: unsure
<222> LOCATION: (618)..(619)
<223> OTHER INFORMATION: n = a, c, g or t
<220> FEATURE:
<221> NAME/KEY: unsure
<222> LOCATION: (639)
<223> OTHER INFORMATION: n = a, c, g or t
<220> FEATURE:
<221> NAME/KEY: unsure
<222> LOCATION: (644)
<223> OTHER INFORMATION: n = a, c, g or t
<220> FEATURE:
<221> NAME/KEY: unsure
<222> LOCATION: (675)
<223> OTHER INFORMATION: n = a, c, g or t

<400> SEQUENCE: 29
aaagaagatc gatcatggct tctatatcct gtctatcctc tttctccctc tccatttct      60 ctgcacctct tcccatttcc atttgttctt catcttccac cttcctaact tcccaaatac    120
catgcaaacc caccaaacgt agcaaaccaa acgccacca cgtttcgaaa gtgacatgca     180
acagtaacca aaacaccca acaccaaacc cagaagaaga aagaccatca tacaacattc    240
taggaaaata tagaagggat gttctccttg cattgggggg cctttacggt gcatctgctc    300
ttagcaacac caacccttta gccatggctg cagctcctat tctagagcct gacctagaac    360
attgttgtat aactgatgat gtaccaccta aaggggtcat cgaggcacaa gtctattgtt    420
gcccaccaag atcttcttcc cctcctatag atttcaagtt gcctaaagga cacccctnan    480
ggttagacca cctgctcaat tcgtcactga tggagtacct agaaaagtag aagttagccc    540
ttaagcgcat ggganagttc catctgatgn tctcgagttc aggaacangn tggtatcaat    600
gggcttntgt gangggggnnt aaacaatagg gtcccaacng agcnaggtta aggtcacttt    660
ctggcggtct ccctncacgt tggac                                          685

<210> SEQ ID NO 30
<211> LENGTH: 179
<212> TYPE: PRT
<213> ORGANISM: Glycine max
<220> FEATURE:
<221> NAME/KEY: UNSURE
<222> LOCATION: (155)..(156)
<223> OTHER INFORMATION: Xaa = any amino acid
<220> FEATURE:
<221> NAME/KEY: UNSURE
<222> LOCATION: (172)
<223> OTHER INFORMATION: Xaa = any amino acid

<400> SEQUENCE: 30

Met Ala Ser Ile Ser Cys Leu Ser Ser Phe Ser Leu Ser Asn Phe Ser
```

```
              1               5              10              15
           Ala Pro Leu Pro Ile Ser Ile Cys Ser Ser Ser Thr Phe Leu Thr
                        20                  25                  30

Ser Gln Ile Pro Cys Lys Pro Thr Lys Arg Ser Lys Pro Lys Arg His
                    35                  40                  45

His Val Ser Lys Val Thr Cys Asn Ser Asn Gln Asn Thr Pro Thr Pro
                50                  55                  60

Asn Pro Glu Glu Arg Pro Ser Tyr Asn Ile Leu Gly Lys Tyr Arg
            65                  70                  75                  80

Arg Asp Val Leu Leu Gly Ile Gly Gly Leu Tyr Gly Ala Ser Ala Leu
                            85                  90                  95

Ser Asn Thr Asn Pro Leu Ala Met Ala Ala Ala Pro Ile Leu Glu Pro
                        100                 105                 110

Asp Leu Glu His Cys Cys Ile Thr Asp Asp Val Pro Pro Lys Gly Val
                        115                 120                 125

Ile Glu Ala Gln Val Tyr Cys Cys Pro Pro Arg Ser Ser Ser Pro Pro
                        130                 135                 140

Ile Asp Phe Lys Leu Pro Lys Gly Thr Pro Xaa Xaa Leu Asp His Leu
           145                 150                 155                 160

Leu Asn Ser Ser Leu Met Glu Tyr Leu Glu Lys Xaa Lys Leu Ala Leu
                            165                 170                 175

Lys Arg Met

<210> SEQ ID NO 31
<211> LENGTH: 1994
<212> TYPE: DNA
<213> ORGANISM: Glycine max

<400> SEQUENCE: 31
gcacgagaaa  gaagaacgat  catggcttat  atctcctctc  tatcatcttt  ctccctctcc    60
aatttctctg  cacctcttcc  catttccatt  tgttcctcat  cttccgcatt  cctaacttcc   120
caaataccat  gcaaaccctc  caaacgtagc  aaaccaaaag  gccatcatgt  ttccaaagtg   180
tcatgcaaca  gtaaccaaaa  cacccccaaca ccaaacccag  aagaagaaaa  accatcgtca   240
tacaacattc  taggaaaaca  taggagggat  attctccttg  gcattggggg  cctttacggt   300
gcttctgctc  ttagcaacac  caaccctttta gccatggctg  cagctcctat  tctagagcct   360
gacctagaac  attgttgtat  aactgatgat  gtacctaaag  gggaaatcga  aaacaagtc    420 tattgttgcc  caccaaaatc  ttcttcccct  cctatagatt  tcaagttgcc  taaggaaca    480 cccettaggg  ttagaccacc  tgctcaattt  gtgaccgatg  agtacctaga  aaagtataag   540
ttagccctta  agcgcatgag  agagcttcca  tctgatgatc  ctcgaagttt  caagcaacaa   600
gctgatatcc  attgtgctta  ttgtgatggt  ggctataagc  aattagggtt  cccagttgag   660
ctagacttca  aagtccactt  ttcatggata  ttttccctt   tccaccgttg  gtacctctat   720
ttctatgagc  gaatcttggg  tagcttgatt  gatgacccaa  cctttgcact  tccatattgg   780
aactgggaca  atcctgatgg  tggcatggta  ttgccttcca  ttttcgcaga  tgaagactcc   840
cctctatatg  accctcgcag  gaatccagac  atcacaccaa  ctactctcgt  agacctaaac   900
tatggcagtg  gaaaggaacc  aagcgtagaa  caaaacctcg  gtgtaatgta  tacgagtgtt   960
gtctctggtg  cgaaacgcgc  atcgctcttc  catggaaaac  catttcttgc  tggaaagcag  1020
cctgagctaa  gtggagggac  cgtagagctt  ggtcctcata  ctgctgtcca  ccgttggacc  1080
ggtgatccaa  gacaacctaa  caaagaggac  atggggaggt  tctattctgc  tggaagagac  1140
```

-continued

```
cccgctttct attctcacca tgccaacgtg gatcgtatgt ggaatatatg gaaaacaata    1200
ccaagtggaa aaagaaggga tttcaaaaac cgtgattggt tggaaacctc ctttttcttc    1260
tacgatgaga acaagaccct tgtccgtgtg aaggtgaaag acagccttga cacgaataag    1320
atgggttatg tttaccaaga tgtcgccatt ccatggctcg agaaaaagcc taaacccaaa    1380
agaactagaa aggctaagaa ggtggcgttc gcacaacaat ttggcggcat tggtgcagca    1440
atggctgctg agactgggcc aagttccaag tttcctctca ctttgttgga ctcaaaggta    1500
accctactag ttaaaaggcc aaagcagttg aggagcaaga gggacaagga ggaagaggaa    1560
gaagtgttgg tgattgatgg gattgagttt gatggggatg atgatgtgaa gtttgatgtc    1620
tatattactg atgaagatgt cgaggatatt ggaccagaga gcacagagtt tgcaggaagc    1680
ttttcgactc tgggtcattc ccattcgaac atgaacatgg acaagaagat caaaactagc    1740
ttgacactgg gaataacaga tttgttagag gacttggatg ctgaaaatga tgatagtgtt    1800
ttggtcacat tggtaccacg atctgagaat gtaaccatca caatccagaa cataaagata    1860
gagtttgaga aggatgagtg aaaatatgtc actcatttac tactaaacat gcaaatgagt    1920
ttccaacatg caaatgagtt taaatttata tcagcatgtt tagcaatttc aaagcaaaaa    1980
aaaaaaaaaa aaaa                                                      1994
```

<210> SEQ ID NO 32
<211> LENGTH: 619
<212> TYPE: PRT
<213> ORGANISM: Glycine max

<400> SEQUENCE: 32

```
Met Ala Tyr Ile Ser Ser Leu Ser Ser Phe Ser Leu Ser Asn Phe Ser
  1               5                  10                  15

Ala Pro Leu Pro Ile Ser Ile Cys Ser Ser Ser Ala Phe Leu Thr
                 20                  25                  30

Ser Gln Ile Pro Cys Lys Pro Ser Lys Arg Ser Lys Pro Lys Gly His
         35                  40                  45

His Val Ser Lys Val Ser Cys Asn Ser Asn Gln Asn Thr Pro Thr Pro
     50                  55                  60

Asn Pro Glu Glu Lys Pro Ser Ser Tyr Asn Ile Leu Gly Lys His
 65                  70                  75                  80

Arg Arg Asp Ile Leu Leu Gly Ile Gly Gly Leu Tyr Gly Ala Ser Ala
                 85                  90                  95

Leu Ser Asn Thr Asn Pro Leu Ala Met Ala Ala Ala Pro Ile Leu Glu
                100                 105                 110

Pro Asp Leu Glu His Cys Cys Ile Thr Asp Asp Val Pro Lys Gly Glu
            115                 120                 125

Ile Glu Lys Gln Val Tyr Cys Cys Pro Pro Lys Ser Ser Ser Pro Pro
        130                 135                 140

Ile Asp Phe Lys Leu Pro Lys Gly Thr Pro Leu Arg Val Arg Pro Pro
145                 150                 155                 160

Ala Gln Phe Val Thr Asp Glu Tyr Leu Glu Lys Tyr Lys Leu Ala Leu
                165                 170                 175

Lys Arg Met Arg Glu Leu Pro Ser Asp Asp Pro Arg Ser Phe Lys Gln
            180                 185                 190

Gln Ala Asp Ile His Cys Ala Tyr Cys Asp Gly Gly Tyr Lys Gln Leu
        195                 200                 205

Gly Phe Pro Val Glu Leu Asp Phe Lys Val His Phe Ser Trp Ile Phe
```

```
            210                 215                 220
Phe Pro Phe His Arg Trp Tyr Leu Tyr Phe Tyr Glu Arg Ile Leu Gly
225                 230                 235                 240
Ser Leu Ile Asp Asp Pro Thr Phe Ala Leu Pro Tyr Trp Asn Trp Asp
                245                 250                 255
Asn Pro Asp Gly Gly Met Val Leu Pro Ser Ile Phe Ala Asp Glu Asp
                260                 265                 270
Ser Pro Leu Tyr Asp Pro Arg Arg Asn Pro Asp Ile Thr Pro Thr Thr
                275                 280                 285
Leu Val Asp Leu Asn Tyr Gly Ser Gly Lys Glu Pro Ser Val Glu Gln
                290                 295                 300
Asn Leu Gly Val Met Tyr Thr Ser Val Val Ser Gly Ala Lys Arg Ala
305                 310                 315                 320
Ser Leu Phe His Gly Lys Pro Phe Leu Ala Gly Lys Gln Pro Glu Leu
                325                 330                 335
Ser Gly Gly Thr Val Glu Leu Gly Pro His Thr Ala Val His Arg Trp
                340                 345                 350
Thr Gly Asp Pro Arg Gln Pro Asn Lys Glu Asp Met Gly Arg Phe Tyr
                355                 360                 365
Ser Ala Gly Arg Asp Pro Ala Phe Tyr Ser His His Ala Asn Val Asp
                370                 375                 380
Arg Met Trp Asn Ile Trp Lys Thr Ile Pro Ser Gly Lys Arg Arg Asp
385                 390                 395                 400
Phe Lys Asn Arg Asp Trp Leu Glu Thr Ser Phe Phe Tyr Asp Glu
                405                 410                 415
Asn Lys Thr Leu Val Arg Val Lys Val Lys Asp Ser Leu Asp Thr Asn
                420                 425                 430
Lys Met Gly Tyr Val Tyr Gln Asp Val Ala Ile Pro Trp Leu Glu Lys
                435                 440                 445
Lys Pro Lys Pro Lys Arg Thr Arg Lys Ala Lys Lys Val Ala Phe Ala
                450                 455                 460
Gln Gln Phe Gly Gly Ile Gly Ala Ala Met Ala Ala Glu Thr Gly Pro
465                 470                 475                 480
Ser Ser Lys Phe Pro Leu Thr Leu Leu Asp Ser Lys Val Thr Leu Leu
                485                 490                 495
Val Lys Arg Pro Lys Gln Leu Arg Ser Lys Arg Asp Lys Glu Glu Glu
                500                 505                 510
Glu Glu Val Leu Val Ile Asp Gly Ile Glu Phe Asp Gly Asp Asp Asp
                515                 520                 525
Val Lys Phe Asp Val Tyr Ile Thr Asp Glu Asp Val Glu Asp Ile Gly
                530                 535                 540
Pro Glu Ser Thr Glu Phe Ala Gly Ser Phe Ser Thr Leu Gly His Ser
545                 550                 555                 560
His Ser Asn Met Asn Met Asp Lys Lys Ile Lys Thr Ser Leu Thr Leu
                565                 570                 575
Gly Ile Thr Asp Leu Leu Glu Asp Leu Asp Ala Glu Asn Asp Asp Ser
                580                 585                 590
Val Leu Val Thr Leu Val Pro Arg Ser Glu Asn Val Thr Ile Thr Ile
                595                 600                 605
Gln Asn Ile Lys Ile Glu Phe Glu Lys Asp Glu
    610                 615

<210> SEQ ID NO 33
```

<211> LENGTH: 2028
<212> TYPE: DNA
<213> ORGANISM: Glycine max

<400> SEQUENCE: 33

| | | | | | |
|---|---|---|---|---|---|
| gcacgagggt | ccctcctgaa | cctgtctgca | tccattccca | tttcttcttc | cgtatgcatg | 60 |
| ttcccaccgt | ctaaaaaacc | tagcaaagca | caaaacggc | gtcatgcttg | ggaagtagca | 120 |
| tgcaatggta | accctagaaa | taggagggac | attctgatcg | gccttggagg | actctatggt | 180 |
| gctacaacaa | gtctcacaag | taacaacact | ggttctgcat | ttggtgcttc | attgtcgcct | 240 |
| ccagatccaa | ctaactgcgt | tcaaccggac | ccagaaaaag | accctttttg | cccaccaccc | 300 |
| cccttcaaag | actacgagct | ccctccacac | gatgacaaga | cattacccct | tcgaattaga | 360 |
| ccagctgctc | atttggtcac | tgatgattac | atagccaagt | acgaggaagc | cgtgaggcgc | 420 |
| atgcaagacc | ttccacctga | tgatcctcgc | agtttcatgc | aacaggccaa | tgtccaccgt | 480 |
| gcctactgcg | atggtcgcgg | ctatactcaa | aagggcttcg | ctgactacaa | gcttgacgtt | 540 |
| cacggctcct | ggatattctt | ccttggcac | cgctggtatc | tctatttcta | tgagaaaatc | 600 |
| ttggggaaga | tgatcggtga | ccccactttc | gctcttccgt | tttggaactg | ggacaatccc | 660 |
| gccggcatga | gaatccctcc | catttttcaca | gacaaaagtt | cgcctctcta | cgacgaacac | 720 |
| aggaatagcg | atcatgtaaa | tgctttcatc | gacctagact | acaagaagga | cgattctcct | 780 |
| gtgaaacctc | ctcaaacaat | tttatggccg | ccagtggaga | aaagaataa | ctcgatcgtc | 840 |
| gacaacttga | tcgtcaacaa | cttgataaaa | gtttatacgg | cagttgcaag | caaaaccaac | 900 |
| tcaagcccag | actacttcct | cgggccagca | ttcgaagctg | gttctgcacc | tcagcaacac | 960 |
| tttggatctc | tggaatcttt | gcacaatact | gtccacagct | ggaccggtga | agagaaaaac | 1020 |
| aatcaccacg | acatggggtt | gttggctacg | gctgcaaaag | atcccatttt | ctttgctcac | 1080 |
| cattcaaacg | tcgataggat | gtggaacata | tggaagacga | aattgctgga | tggaagaaga | 1140 |
| tttgatcaca | aaagtgacga | ctggttggaa | tccagtttct | tcttctacga | cgagaacaag | 1200 |
| aactatgtgc | gtgtgaaggt | caagactgc | ctcgactcca | gaagatggg | gtatgattac | 1260 |
| caacgtgttg | accttccatg | gctgttggct | ggggaactca | tcaaaccaaa | gaaggagatt | 1320 |
| attctccttc | gttcaaaacc | agaagcttca | acattcaaga | cattacagct | ccctctccct | 1380 |
| ctggaatcca | ttgagcgtac | aaacgtgaag | aggccgaagc | cgcgatccag | gaacgagaat | 1440 |
| gaagaagaag | aagaaggcgt | agaagaggtg | ttagtgatag | atgttgagta | cgatagcact | 1500 |
| gatggtgtga | ggtttgatgt | gttcatcaac | gaccaaggcg | acaatgagat | tggaccccag | 1560 |
| gattcagagt | ttgcgggaag | ctttgtgact | ttgcctcact | cgccgcatgt | caaccataac | 1620 |
| aacatcacca | agcttctttt | caaattgcca | ttaacgtata | agttgaaaga | cttgggagta | 1680 |
| acaaaagacg | atgatagtat | ttctgtcaca | ctggctccca | tatatgggga | caagcctgtt | 1740 |
| acaattaagg | acgtaaggat | aaagcgtgtt | tatcctgagg | tggacgatga | ataaatctaa | 1800 |
| attatgtgtg | tgctactgct | agggtttgtt | cctccaaggg | atactctatc | tgtcatttgt | 1860 |
| tgtttcttaa | ttagtgtgtt | gtagttattt | tccttggaac | ttaatagatc | cctttcatct | 1920 |
| gtgagggata | ctatgttatt | gttataataa | atgtttgttt | tattgttaca | tttgtttata | 1980 |
| atacaatata | actcctaatc | tccttttaaa | aaaaaaaaa | aaaaaaaa | | 2028 |

<210> SEQ ID NO 34
<211> LENGTH: 597
<212> TYPE: PRT
<213> ORGANISM: Glycine max

<400> SEQUENCE: 34

```
Ala Arg Gly Ser Leu Leu Asn Leu Ser Ala Ser Ile Pro Ile Ser Ser
  1               5                  10                  15

Ser Val Cys Met Phe Pro Ser Lys Lys Pro Ser Lys Ala Thr Lys
             20                  25                  30

Arg Arg His Ala Trp Glu Val Ala Cys Asn Gly Asn Pro Arg Asn Arg
             35                  40                  45

Arg Asp Ile Leu Ile Gly Leu Gly Leu Tyr Gly Ala Thr Thr Ser
         50                  55                  60

Leu Thr Ser Asn Asn Thr Gly Ser Ala Phe Gly Ala Ser Leu Ser Pro
 65                  70                  75                  80

Pro Asp Pro Thr Asn Cys Val Gln Pro Asp Pro Glu Lys Asp Pro Phe
                 85                  90                  95

Cys Pro Pro Pro Phe Lys Asp Tyr Glu Leu Pro Pro His Asp Asp
                100                 105                 110

Lys Thr Leu Pro Leu Arg Ile Arg Pro Ala Ala His Leu Val Thr Asp
            115                 120                 125

Asp Tyr Ile Ala Lys Tyr Glu Glu Ala Val Arg Arg Met Gln Asp Leu
        130                 135                 140

Pro Pro Asp Asp Pro Arg Ser Phe Met Gln Gln Ala Asn Val His Arg
145                 150                 155                 160

Ala Tyr Cys Asp Gly Arg Gly Tyr Thr Gln Lys Gly Phe Ala Asp Tyr
                165                 170                 175

Lys Leu Asp Val His Gly Ser Trp Ile Phe Phe Pro Trp His Arg Trp
            180                 185                 190

Tyr Leu Tyr Phe Tyr Glu Lys Ile Leu Gly Lys Met Ile Gly Asp Pro
        195                 200                 205

Thr Phe Ala Leu Pro Phe Trp Asn Trp Asp Asn Pro Ala Gly Met Arg
    210                 215                 220

Ile Pro Pro Ile Phe Thr Asp Lys Ser Ser Pro Leu Tyr Asp Glu His
225                 230                 235                 240

Arg Asn Ser Asp His Val Asn Ala Phe Ile Asp Leu Asp Tyr Lys Lys
                245                 250                 255

Asp Asp Ser Pro Val Lys Pro Pro Gln Thr Ile Leu Trp Pro Pro Val
            260                 265                 270

Glu Lys Lys Asn Asn Ser Ile Val Asp Asn Leu Ile Val Asn Asn Leu
        275                 280                 285

Ile Lys Val Tyr Thr Ala Val Ala Ser Lys Thr Asn Ser Ser Pro Asp
    290                 295                 300

Tyr Phe Leu Gly Pro Ala Phe Glu Ala Gly Ser Ala Pro Gln Gln His
305                 310                 315                 320

Phe Gly Ser Leu Glu Ser Leu His Asn Thr Val His Ser Trp Thr Gly
                325                 330                 335

Glu Arg Glu Asn Asn His His Asp Met Gly Leu Leu Ala Thr Ala Ala
            340                 345                 350

Lys Asp Pro Ile Phe Phe Ala His His Ser Asn Val Asp Arg Met Trp
        355                 360                 365

Asn Ile Trp Lys Thr Glu Leu Leu Asp Gly Arg Arg Phe Asp His Lys
    370                 375                 380

Ser Asp Asp Trp Leu Glu Ser Phe Phe Tyr Asp Glu Asn Lys
385                 390                 395                 400

Asn Tyr Val Arg Val Lys Val Lys Asp Cys Leu Asp Ser Lys Lys Met
```

```
                      405                 410                 415
Gly Tyr Asp Tyr Gln Arg Val Asp Leu Pro Trp Leu Leu Ala Gly Glu
                420                 425                 430
Leu Ile Lys Pro Lys Glu Ile Ile Leu Leu Arg Ser Lys Pro Glu
            435                 440                 445
Ala Ser Thr Phe Lys Thr Leu Gln Leu Pro Leu Pro Leu Glu Ser Ile
        450                 455                 460
Glu Arg Thr Asn Val Lys Arg Pro Lys Pro Arg Ser Arg Asn Glu Asn
465                 470                 475                 480
Glu Glu Glu Glu Gly Val Glu Glu Val Leu Val Ile Asp Val Glu
                485                 490                 495
Tyr Asp Ser Thr Asp Gly Val Arg Phe Asp Val Phe Ile Asn Asp Gln
            500                 505                 510
Gly Asp Asn Glu Ile Gly Pro Gln Asp Ser Glu Phe Ala Gly Ser Phe
        515                 520                 525
Val Thr Leu Pro His Ser Pro His Val Asn His Asn Asn Ile Thr Lys
        530                 535                 540
Ala Ser Phe Lys Leu Pro Leu Thr Tyr Lys Leu Lys Asp Leu Gly Val
545                 550                 555                 560
Thr Lys Asp Asp Asp Ser Ile Ser Val Thr Leu Ala Pro Ile Tyr Gly
                565                 570                 575
Asp Lys Pro Val Thr Ile Lys Asp Val Arg Ile Lys Arg Val Tyr Pro
            580                 585                 590
Glu Val Asp Asp Glu
        595

<210> SEQ ID NO 35
<211> LENGTH: 2260
<212> TYPE: DNA
<213> ORGANISM: Glycine max

<400> SEQUENCE: 35
ccttgaggag tatcactagt tcggcagcgg cgccaccgcg gtgaacaccc cgggctgcag      60
gaattcggca cgagaatgag tactccttct aagcttttat ctttattctt tgtactcatt     120
gtcttgctga tgcccttagt ttccttactc aacaatgatt tctctatctt caccattaaa     180
accatttcat acctagtttc ctttagtgaa agccaaacc attactctaa tttcagcatt      240
attccataca aagcccaaaa tagtaaacaa aatggccaca tcaccacaaa ctccaatgga     300
agagacaaac cacgtctttg gaggaaagcc ttcattggct tcaaaaatac tcacgagcca     360
tcttcgaata tttctcgagc aatatccctt aatgtaagca agtgttttcc cgttgagtta     420
ccttcttttg caataaccaa ttcccattgt tgtccaccta gaccacctcc ttctaagatc     480
atagatttca aagattttgc ttctccaaac gccacgcttc gagtaagaaa accggctcac     540
atggtagatg aggagtacat agcaaaactt gaaagggca ttgcactcat gaaagcactc      600
cctgatgatg acccacgtaa tttcatacaa caagcaaagg tccattgtgc ttattgtaac     660
ggtgcctatc acctaccca tcccttcag aacacaaaac tcaacattca caggtcttgg      720
tttttctttc ctttccaccg ttggtacatt tacttcttcg agcgaatctt gggaagcttg     780
ctcggtgacc cgaactttgc cttaccgttt tggaattggg atgctgtaga agggatgcaa     840
atgccaccat atttcgcaaa ccctaactcg tcgctctatc acaaactccg aaacccaag      900 cacttgccac cgcaagtggt tgacctgaac tatgatccat tgactttaa tgatgataca      960 ccttctcatc aacaagtttc gtataatcta gccttcatgt acaagcaaat ggtgctagca    1020
```

-continued

```
agtaccaaag aattgttcat gggaagccct tttcgactcg gcgataaccc tactccggt     1080 attggctcta tagaggctgc tcctcataac acggttcata aatgggttgg tgctgctgat     1140
aagccacacc aggaggacat gggaacgttc tacacagctg ctagagatcc cgttttctat     1200
ccgcatcaca cgaactcgga tcgactgtgg gggatatgga aaaaattggg agaaggaaga     1260
aaggactata gtgatgatcc agattggtta gattctgatt tttacttcta tgatgagaat     1320
gccaattttg ttcgcgtgaa ggtaagagat tgctttgata ctaaaagatt ggggtatgtt     1380
tacgaagatg ttgatcttcc atggttgcga acgccaccca catcgcgaaa aagcaagcta     1440
ctaagagaag ccaaaaaggg ttcacttttg agttcaaagc catggaaatt cctttggtt      1500 ttggattcca taacgagtat tgttgttaag aggccgaaga atggaggag caaggaggag      1560 aaagaacaag aggaggaggt tttggtgata aagggattg agtttggaag tgataaatat      1620
gtcaagtttg atgttcatat tgatgatgat gaagacaatt tgagtggtcc ggatgagaca     1680
gagtttgtgg aagttttgt gaatgtgcag catgggcatg ccataatgt caaaactagc      1740 tttaaggtag ggatatcgaa agtgctggag agtgtagaag ctgaagaaga cgatgaggtg     1800
ctggtttctt tggtacctaa ggtgggaaaa ggggatgcca taataggag catcaaaatt      1860 gagtttattc caaatactta ggattatttt gtgggtgtga aaattttaca cttttacaa      1920 gttttgttgt ttatgctttt aaaaggtagt tttttttttt tccttttttt agtgtagcaa     1980
gtcgagctcg tattctctgt ggctggattt tgtccaacta actgaaatat gagatgtcga     2040
atttgctata tattttacag caattgggga agggaaagaa tgtgaaggaa gttgaaattt     2100
tggatgtggg gaagtactcc tagaagtaga tataaatttg ttgtggtgca tgtctttcaa     2160
cactagtgca tgtaaagaaa atcaaataaa tcaatttgat tttctagaac taattttcat     2220
aataaaaaat tgagtttgat gtaaaaaaaa aaaaaaaaa                           2260
```

<210> SEQ ID NO 36
<211> LENGTH: 601
<212> TYPE: PRT
<213> ORGANISM: Glycine max

<400> SEQUENCE: 36

```
Met Ser Thr Pro Ser Lys Leu Leu Ser Leu Phe Phe Val Leu Ile Val
 1               5                  10                  15

Leu Leu Met Pro Leu Val Ser Leu Asn Asn Asp Phe Ser Ile Phe
            20                  25                  30

Thr Ile Lys Thr Ile Ser Tyr Leu Val Ser Phe Ser Glu Lys Pro Asn
        35                  40                  45

His Tyr Ser Asn Phe Ser Ile Ile Pro Tyr Lys Ala Gln Asn Ser Lys
    50                  55                  60

Gln Asn Gly His Ile Thr Thr Asn Ser Asn Gly Arg Asp Lys Pro Arg
65                  70                  75                  80

Leu Trp Arg Lys Ala Phe Ile Gly Phe Lys Asn Thr His Glu Pro Ser
                85                  90                  95

Ser Asn Ile Ser Arg Ala Ile Ser Leu Asn Val Ser Lys Cys Phe Pro
            100                 105                 110

Val Glu Leu Pro Ser Phe Ala Ile Thr Asn Ser His Cys Cys Pro Pro
        115                 120                 125

Arg Pro Pro Pro Ser Lys Ile Ile Asp Phe Lys Asp Phe Ala Ser Pro
    130                 135                 140

Asn Ala Thr Leu Arg Val Arg Lys Pro Ala His Met Val Asp Glu Glu
```

-continued

```
                145                 150                 155                 160

Tyr Ile Ala Lys Leu Glu Lys Gly Ile Ala Leu Met Lys Ala Leu Pro
                    165                 170                 175

Asp Asp Pro Arg Asn Phe Ile Gln Gln Ala Lys Val His Cys Ala
                180                 185                 190

Tyr Cys Asn Gly Ala Tyr His Leu Pro His Pro Phe Gln Asn Thr Lys
            195                 200                 205

Leu Asn Ile His Arg Ser Trp Phe Phe Pro Phe His Arg Trp Tyr
        210                 215                 220

Ile Tyr Phe Phe Glu Arg Ile Leu Gly Ser Leu Leu Gly Asp Pro Asn
225                 230                 235                 240

Phe Ala Leu Pro Phe Trp Asn Trp Asp Ala Val Glu Gly Met Gln Met
                245                 250                 255

Pro Pro Tyr Phe Ala Asn Pro Asn Ser Ser Leu Tyr His Lys Leu Arg
                260                 265                 270

Asn Pro Lys His Leu Pro Pro Gln Val Val Asp Leu Asn Tyr Asp Pro
            275                 280                 285

Phe Asp Phe Asn Asp Asp Thr Pro Ser His Gln Gln Val Ser Tyr Asn
        290                 295                 300

Leu Ala Phe Met Tyr Lys Gln Met Val Leu Ala Ser Thr Lys Glu Leu
305                 310                 315                 320

Phe Met Gly Ser Pro Phe Arg Leu Gly Asp Asn Pro Thr Pro Gly Ile
                325                 330                 335

Gly Ser Ile Glu Ala Ala Pro His Asn Thr Val His Lys Trp Val Gly
                340                 345                 350

Ala Ala Asp Lys Pro His Gln Glu Asp Met Gly Thr Phe Tyr Thr Ala
                355                 360                 365

Ala Arg Asp Pro Val Phe Tyr Pro His His Thr Asn Ser Asp Arg Leu
        370                 375                 380

Trp Gly Ile Trp Lys Lys Leu Gly Glu Gly Arg Lys Asp Tyr Ser Asp
385                 390                 395                 400

Asp Pro Asp Trp Leu Asp Ser Asp Phe Tyr Phe Tyr Asp Glu Asn Ala
                405                 410                 415

Asn Phe Val Arg Val Lys Val Arg Asp Cys Phe Asp Thr Lys Arg Leu
                420                 425                 430

Gly Tyr Val Tyr Glu Asp Val Asp Leu Pro Trp Leu Arg Thr Pro Pro
            435                 440                 445

Thr Ser Arg Lys Ser Lys Leu Leu Arg Glu Ala Lys Lys Gly Ser Leu
        450                 455                 460

Leu Ser Ser Lys Pro Trp Lys Phe Pro Leu Val Leu Asp Ser Ile Thr
465                 470                 475                 480

Ser Ile Val Val Lys Arg Pro Lys Lys Trp Arg Ser Lys Glu Glu Lys
                485                 490                 495

Glu Gln Glu Glu Val Leu Val Ile Glu Gly Ile Glu Phe Gly Ser
            500                 505                 510

Asp Lys Tyr Val Lys Phe Asp Val His Ile Asp Asp Glu Asp Asn
        515                 520                 525

Leu Ser Gly Pro Asp Glu Thr Glu Phe Val Gly Ser Phe Val Asn Val
        530                 535                 540

Gln His Gly His Gly His Asn Val Lys Thr Ser Phe Lys Val Gly Ile
545                 550                 555                 560

Ser Lys Val Leu Glu Ser Val Glu Ala Glu Glu Asp Asp Glu Val Leu
                565                 570                 575
```

```
Val Ser Leu Val Pro Lys Val Gly Lys Gly Asp Ala Ile Ile Gly Gly
            580                 585                 590

Ile Lys Ile Glu Phe Ile Pro Lys Tyr
            595                 600

<210> SEQ ID NO 37
<211> LENGTH: 1141
<212> TYPE: DNA
<213> ORGANISM: Zea mays
<220> FEATURE:
<221> NAME/KEY: unsure
<222> LOCATION: (16)
<223> OTHER INFORMATION: n = a, c, g or t
<220> FEATURE:
<221> NAME/KEY: unsure
<222> LOCATION: (60)
<223> OTHER INFORMATION: n = a, c, g or t

<400> SEQUENCE: 37
ccgacaaccc gctgtncgac ccctaccgca acatggagaa catggacgcc ctgctcgatn     60
tggactacct caagaaaccc agacgcgaca ccatcccttt cgagccgccg acggacccag    120
ccgcgcgcgc caagtacgac gacgccgttc aaaccaacct gtgcaccata tacctgcagc    180
aagtccgtga cggcaagggc ccccgtgctt tcctcggcga aagctgtgc agcgaccagg     240
gcacgctgga gcggatggcg cacacgacgg tgcacgtgtg acggggcgg gcgaacccgg     300
cgacgtgcag cgcggagcag ggcggcgtgg tggggcacga cggcaagccg cactgccagg    360
tggacatggg gttcctgggc acggcgggc gtgacccgct cttctactcg caccacgcga    420
acgtggaccg catgtggcac atctggtcca ctaggctggg cggtaagggc ttcgacgacc    480
cggagtggct ggacaccagc ttcgtgttct acgacgacta ccggagccgc ggctggtgac    540
agatgaagtt ccgcgacgtc ctgaacgcga ccaggctcgg gtacacgtac gacaaggagt    600
cggaggcggc gctgccgtgg ctgaacagca agccgacccg gttctccggc ggcggcaagg    660
cgaaggcgaa ggcggcgccc aaggtggcgt cggagttccc gctgaccctg acggacgagg    720
ccgtggacgt gccggcggtg gcggtcccgg cgcggcaggc cgggaaggac ctggtgctgc    780
tgatcgaggg catcgagtac gacccccaga tcaacaacaa gttcgacgtg gtcatcaacg    840
tggcccggga ggacgccgcg agggtggggc ctaaggacag cgagtacgcc ggcagcttca    900
gcgccgtgcc cagctccaac gccgccggtg gcacgctggt gggcaagttc acgctcgccc    960
tcgacggcgt gctcgccgac ctcgggctcg ccggcgcgag cgccgtcgac atcgtgctcg   1020
tccctcacac ggagggcgag atcaagctgt acttgccccc gaccatcgag aacgcgtgag   1080
aactgagatg agatgagacc cgccacgcac tggctggctg gctgttcgtc tgtccaccgt   1140
c                                                                  1141

<210> SEQ ID NO 38
<211> LENGTH: 358
<212> TYPE: PRT
<213> ORGANISM: Zea mays
<220> FEATURE:
<221> NAME/KEY: UNSURE
<222> LOCATION: (5)
<223> OTHER INFORMATION: Xaa = any amino acid
<220> FEATURE:
<221> NAME/KEY: UNSURE
<222> LOCATION: (20)
<223> OTHER INFORMATION: Xaa = any amino acid
<220> FEATURE:
<221> NAME/KEY: UNSURE
<222> LOCATION: (179)
```

<223> OTHER INFORMATION: Xaa = any amino acid

<400> SEQUENCE: 38

```
Asp Asn Pro Leu Xaa Asp Pro Tyr Arg Asn Met Glu Asn Met Asp Ala
 1               5                  10                  15

Leu Leu Asp Xaa Asp Tyr Leu Lys Lys Pro Arg Arg Asp Thr Ile Pro
            20                  25                  30

Phe Glu Pro Pro Thr Asp Pro Ala Ala Arg Ala Lys Tyr Asp Asp Ala
        35                  40                  45

Val Gln Thr Asn Leu Cys Thr Ile Tyr Leu Gln Gln Val Arg Asp Gly
     50                  55                  60

Lys Gly Pro Arg Ala Phe Leu Gly Glu Lys Leu Cys Ser Asp Gln Gly
 65                  70                  75                  80

Thr Leu Glu Arg Met Ala His Thr Thr Val His Val Trp Thr Gly Arg
                85                  90                  95

Ala Asn Pro Ala Thr Cys Ser Ala Glu Gln Gly Val Val Gly His
            100                 105                 110

Asp Gly Lys Pro His Cys Gln Val Asp Met Gly Phe Leu Gly Thr Ala
        115                 120                 125

Gly Arg Asp Pro Leu Phe Tyr Ser His His Ala Asn Val Asp Arg Met
130                 135                 140

Trp His Ile Trp Ser Thr Arg Leu Gly Gly Lys Gly Phe Asp Asp Pro
145                 150                 155                 160

Glu Trp Leu Asp Thr Ser Phe Val Phe Tyr Asp Asp Tyr Arg Ser Arg
                165                 170                 175

Gly Trp Xaa Gln Met Lys Phe Arg Asp Val Leu Asn Ala Thr Arg Leu
            180                 185                 190

Gly Tyr Thr Tyr Asp Lys Glu Ser Glu Ala Ala Leu Pro Trp Leu Asn
        195                 200                 205

Ser Lys Pro Thr Arg Phe Ser Gly Gly Lys Ala Lys Ala Lys Ala
210                 215                 220

Ala Pro Lys Val Ala Ser Glu Phe Pro Leu Thr Leu Thr Asp Glu Ala
225                 230                 235                 240

Val Asp Val Pro Ala Val Ala Val Pro Ala Arg Gln Ala Gly Lys Asp
                245                 250                 255

Leu Val Leu Leu Ile Glu Gly Ile Glu Tyr Asp Pro Gln Ile Asn Asn
            260                 265                 270

Lys Phe Asp Val Val Ile Asn Val Ala Arg Glu Asp Ala Ala Arg Val
        275                 280                 285

Gly Pro Lys Asp Ser Glu Tyr Ala Gly Ser Phe Ser Ala Val Pro Ser
290                 295                 300

Ser Asn Ala Ala Gly Gly Thr Leu Val Gly Lys Phe Thr Leu Ala Leu
305                 310                 315                 320

Asp Gly Val Leu Ala Asp Leu Gly Leu Ala Gly Ala Ser Ala Val Asp
                325                 330                 335

Ile Val Leu Val Pro His Thr Gly Glu Ile Lys Leu Tyr Leu Pro
            340                 345                 350

Pro Thr Ile Glu Asn Ala
        355
```

<210> SEQ ID NO 39
<211> LENGTH: 2173
<212> TYPE: DNA
<213> ORGANISM: Zea mays

<400> SEQUENCE: 39

```
gcgtggcaac gtccaaaatc cagaccgctg gtaggagtat ctcgtagaca ttgaacaacg      60
gctgcatggc gagcgcctgc gccacctcca tccccctcgt ctcggcgccc tctgcatgcc     120
cgtccaagaa gaccaccgtc gccaggttcc ggcgccgcac ggcgacgtgc agggccagca     180
gcggcggtgg cggtggccgg ggcggcgaaa atgatggcct cctttggctg ccccggcggg     240
acgtgatgct caacggcctg tccagtgtcg ccgccgggct cgcctggtac ccgggcgtcg     300
cgtccggcgc ggatgcggtg tgcaccaggg ccgacaaggt gaacgagaag accgtgcagt     360
gcacggaccc ggccgggcag cttccgtgcc ctctggtgtc gccgacggac cccgtggact     420
tcaagccgga aagcaaggtg acgcgcatcc ggcagccggt gcatctcctg agccgggagt     480
accaggagaa gtacaaggag gccgtcgcga agatgaaggc gctaccggaa gagaacccgc     540
tgagcttcgc ggcccaggcg gccatccacc aggcttactg cgacgcctac tacaagtacg     600
acccgacggc caaggacgcg ccgttcgacg tgcacttctc gtggatcttc gcgccgtggc     660
accgcatgta catctacttc tacgagcgcg ccctcgggca gctcatcggc gacgacacct     720
tcgcgctgcc gttctggaac tgggacacgc cggccggcat ggtggtgccg ccactcttca     780
aggactccat gggcaacccg ctgtacgacc ccaacaggaa cccgtcgaac gtcgacgcgc     840
tggtggactt agactacctc aacgacagga atgcggagcc catcccttc aagggcccac     900
gggacgaaaa gtacaaggaa cttgtgaaca agaacctgtg caccgtatac acccagcaaa     960
tacgtagcgg caagggcgcc gagtcgttcc tgggcgagaa gtactgcacc gacatcgggt    1020
caagcacgag cagcatgggt tcgctggagc ggatggcgca cactgccgtg cacgtctggg    1080
tcggcaaggc gggcccgacg ccttcctcgg aggcgtgcag tgccgctacc ggcggcttcc    1140
cgaaccacac caaaggcggg tacagctgca acaacgacat ggggttcctg ggtcggcgg    1200
gacacgaccc gctcttctac tcgcaccact ccaacgtcga ccgcatgtgg cacatctggt    1260
cgaccaggct cggcggcggg cagggcatca cggaggcgga ctggctcgac accagcttcg    1320
tcttctacga cgacgtcaag agcccgcgga aggtgcgcat caggttccgc gacgtcctgg    1380
acacgcgcga cctcggctac acgtacgacg ccgagtccga caaggacctg ccatggctgc    1440
gctgcaagat ctcgtcgctg gtgccccacg gcaaggacag cccgccgagg tcgtcgtcgg    1500
caaggaaggc ggcgccggtg ttcccgctcg ccctgactaa gggccaggtg gtggaagtgc    1560
cggccgtgcc tgtgccggcc aaggaccccg ggaaggagca gctgctggtg atcgagggca    1620
tcgagtacga ccccccaggcg aacaataagt tcgacgtcgc catcaacctg cccgcggaca    1680
aagcgttgca ggtaggccca cagtacaagg agtacgccgg aagcttcgcc gtcgtgccgg    1740
gctccggcgc cgggaagacg cggaaagtga agctctccct gtgcatcacc gaagtgctgt    1800
tcgatatcga cgctgacggc gataaaaccg tcgacgtcgt tatcgtgccg cgcacaaatg    1860
ctaagatcac gctcaacgct cgccccacca tcaagaatcg gaactaggag ctagttgcta    1920
ctagtgctca tcaagcacac tgtacgtacg tacgtatgta ctcgatcgcg tggtcattca    1980
tcgaccatca tcgtttatat gctgtcacgc acagcgcggg ccggccggta gggtgtcggc    2040
aataataaac gcggccagtg ttgcattatt gtgtgtttta tttcacaagg attaggagcg    2100
agccaatggt agattctaag gaataaataa cattgttatg aatgatatgg ttatgtttta    2160
gagactaatt gcg                                                       2173
```

<210> SEQ ID NO 40
<211> LENGTH: 613

```
<212> TYPE: PRT
<213> ORGANISM: Zea mays

<400> SEQUENCE: 40
```

| | | | | | | | | | | | | | | |
|---|---|---|---|---|---|---|---|---|---|---|---|---|---|---|
|Met|Ala|Ser|Ala|Cys|Ala|Thr|Ser|Ile|Pro|Leu|Val|Ser|Ala|Pro|Ser|
|1| | | |5| | | | |10| | | | |15|

Ala Cys Pro Ser Lys Lys Thr Thr Val Ala Arg Phe Arg Arg Arg Thr
             20                  25                  30

Ala Thr Cys Arg Ala Ser Ser Gly Gly Gly Gly Arg Gly Gly Glu
         35                  40                  45

Asn Asp Gly Leu Leu Trp Leu Pro Arg Arg Asp Val Met Leu Asn Gly
         50                  55                  60

Leu Ser Ser Val Ala Ala Gly Leu Ala Trp Tyr Pro Gly Val Ala Ser
65                  70                  75                  80

Gly Ala Asp Ala Val Cys Thr Arg Ala Asp Lys Val Asn Glu Lys Thr
                 85                  90                  95

Val Gln Cys Thr Asp Pro Ala Gly Gln Leu Pro Cys Pro Leu Val Ser
             100                 105                 110

Pro Thr Asp Pro Val Asp Phe Lys Pro Glu Ser Lys Val Thr Arg Ile
         115                 120                 125

Arg Gln Pro Val His Leu Leu Ser Arg Glu Tyr Gln Glu Lys Tyr Lys
130                 135                 140

Glu Ala Val Ala Lys Met Lys Ala Leu Pro Glu Glu Asn Pro Leu Ser
145                 150                 155                 160

Phe Ala Ala Gln Ala Ala Ile His Gln Ala Tyr Cys Asp Ala Tyr Tyr
                 165                 170                 175

Lys Tyr Asp Pro Thr Ala Lys Asp Ala Pro Phe Asp Val His Phe Ser
             180                 185                 190

Trp Ile Phe Ala Pro Trp His Arg Met Tyr Ile Tyr Phe Tyr Glu Arg
         195                 200                 205

Ala Leu Gly Gln Leu Ile Gly Asp Asp Thr Phe Ala Leu Pro Phe Trp
210                 215                 220

Asn Trp Asp Thr Pro Ala Gly Met Val Val Pro Pro Leu Phe Lys Asp
225                 230                 235                 240

Ser Met Gly Asn Pro Leu Tyr Asp Pro Asn Arg Asn Pro Ser Asn Val
                 245                 250                 255

Asp Ala Leu Val Asp Leu Asp Tyr Leu Asn Asp Arg Asn Ala Glu Pro
             260                 265                 270

Ile Pro Phe Lys Gly Pro Arg Asp Glu Lys Tyr Lys Glu Leu Val Asn
         275                 280                 285

Lys Asn Leu Cys Thr Val Tyr Thr Gln Gln Ile Arg Ser Gly Lys Gly
         290                 295                 300

Ala Glu Ser Phe Leu Gly Glu Lys Tyr Cys Thr Asp Ile Gly Ser Ser
305                 310                 315                 320

Thr Ser Ser Met Gly Ser Leu Glu Arg Met Ala His Thr Ala Val His
                 325                 330                 335

Val Trp Val Gly Lys Ala Gly Pro Thr Pro Ser Ser Glu Ala Cys Ser
             340                 345                 350

Ala Ala Thr Gly Gly Phe Pro Asn His Thr Lys Gly Gly Tyr Ser Cys
         355                 360                 365

Asn Asn Asp Met Gly Phe Leu Gly Ser Ala Gly His Asp Pro Leu Phe
         370                 375                 380

Tyr Ser His His Ser Asn Val Asp Arg Met Trp His Ile Trp Ser Thr
385                 390                 395                 400

```
Arg Leu Gly Gly Gly Gln Gly Ile Thr Glu Ala Asp Trp Leu Asp Thr
                405                 410                 415
Ser Phe Val Phe Tyr Asp Asp Val Lys Ser Pro Arg Lys Val Arg Ile
            420                 425                 430
Arg Phe Arg Asp Val Leu Asp Thr Arg Asp Leu Gly Tyr Thr Tyr Asp
        435                 440                 445
Ala Glu Ser Asp Lys Asp Leu Pro Trp Leu Arg Cys Lys Ile Ser Ser
    450                 455                 460
Leu Val Pro His Gly Lys Asp Ser Pro Arg Ser Ser Ala Arg
465                 470                 475                 480
Lys Ala Ala Pro Val Phe Pro Leu Ala Leu Thr Lys Gly Gln Val Val
                485                 490                 495
Glu Val Pro Ala Val Pro Val Pro Ala Lys Asp Pro Gly Lys Glu Gln
            500                 505                 510
Leu Leu Val Ile Glu Gly Ile Glu Tyr Asp Pro Gln Ala Asn Asn Lys
        515                 520                 525
Phe Asp Val Ala Ile Asn Leu Pro Ala Asp Lys Ala Leu Gln Val Gly
    530                 535                 540
Pro Gln Tyr Lys Glu Tyr Ala Gly Ser Phe Ala Val Val Pro Gly Ser
545                 550                 555                 560
Gly Ala Gly Lys Thr Arg Lys Val Lys Leu Ser Leu Cys Ile Thr Glu
                565                 570                 575
Val Leu Phe Asp Ile Asp Ala Asp Gly Asp Lys Thr Val Asp Val Val
            580                 585                 590
Ile Val Pro Arg Thr Asn Ala Lys Ile Thr Leu Asn Ala Arg Pro Thr
        595                 600                 605
Ile Lys Asn Arg Asn
    610

<210> SEQ ID NO 41
<211> LENGTH: 409
<212> TYPE: DNA
<213> ORGANISM: Zea mays
<220> FEATURE:
<221> NAME/KEY: unsure
<222> LOCATION: (409)
<223> OTHER INFORMATION: n = a, c, g or t

<400> SEQUENCE: 41
ccagctgatt tgtccacgcg gcatggcgac ggccagcgcc gcttcaagct tcctcgtccc     60
ggcgactgct atcgccccga cccctctgc atgcccatcc acggttccca agaacaagaa    120
gaatgctgcc ggccggcggc ggcgcacatt gcagtgcagg ccagcggcc ggcggggcga    180 cgacgaagac agccgcctcc tctggctgcc ccggcgggaa gtgctgaccg gtctgggcgg    240
cgtggccgcc agcttcgtcg ggtacccgga tctggcttcc atcgccctgg aagcgaaccc    300
cgtggagagc tgccggcggg gcgagaaggt gacggagaag ctggtggagt gctcggaccc    360
gaacagagac ttcccgtgcc cgccggcgtc acgggtcccc atcgtggan               409

<210> SEQ ID NO 42
<211> LENGTH: 123
<212> TYPE: PRT
<213> ORGANISM: Zea mays

<400> SEQUENCE: 42

Met Ala Thr Ala Ser Ala Ala Ser Ser Phe Leu Val Pro Ala Thr Ala
 1               5                  10                  15
```

```
Ile Ala Pro Thr Pro Ser Ala Cys Pro Ser Thr Val Pro Lys Asn Lys
            20                  25                  30

Lys Asn Ala Ala Gly Arg Arg Arg Thr Leu Gln Cys Arg Ala Ser
        35                  40                  45

Gly Arg Arg Gly Asp Asp Glu Asp Ser Arg Leu Leu Trp Leu Pro Arg
    50                  55                  60

Arg Glu Val Leu Thr Gly Leu Gly Gly Val Ala Ala Ser Phe Val Gly
65                  70                  75                  80

Tyr Pro Asp Leu Ala Ser Ile Ala Leu Glu Ala Asn Pro Val Glu Ser
                85                  90                  95

Cys Arg Arg Gly Glu Lys Val Thr Glu Lys Leu Val Glu Cys Ser Asp
            100                 105                 110

Pro Asn Arg Asp Phe Pro Cys Pro Pro Ala Ser
            115                 120
```

<210> SEQ ID NO 43
<211> LENGTH: 497
<212> TYPE: DNA
<213> ORGANISM: Glycine max
<220> FEATURE:
<221> NAME/KEY: unsure
<222> LOCATION: (325)
<223> OTHER INFORMATION: n = a, c, g or t
<220> FEATURE:
<221> NAME/KEY: unsure
<222> LOCATION: (397)
<223> OTHER INFORMATION: n = a, c, g or t
<220> FEATURE:
<221> NAME/KEY: unsure
<222> LOCATION: (411)
<223> OTHER INFORMATION: n = a, c, g or t
<220> FEATURE:
<221> NAME/KEY: unsure
<222> LOCATION: (422)
<223> OTHER INFORMATION: n = a, c, g or t
<220> FEATURE:
<221> NAME/KEY: unsure
<222> LOCATION: (438)
<223> OTHER INFORMATION: n = a, c, g or t
<220> FEATURE:
<221> NAME/KEY: unsure
<222> LOCATION: (441)
<223> OTHER INFORMATION: n = a, c, g or t
<220> FEATURE:
<221> NAME/KEY: unsure
<222> LOCATION: (453)
<223> OTHER INFORMATION: n = a, c, g or t
<220> FEATURE:
<221> NAME/KEY: unsure
<222> LOCATION: (463)
<223> OTHER INFORMATION: n = a, c, g or t
<220> FEATURE:
<221> NAME/KEY: unsure
<222> LOCATION: (467)
<223> OTHER INFORMATION: n = a, c, g or t
<220> FEATURE:
<221> NAME/KEY: unsure
<222> LOCATION: (477)
<223> OTHER INFORMATION: n = a, c, g or t
<220> FEATURE:
<221> NAME/KEY: unsure
<222> LOCATION: (487)
<223> OTHER INFORMATION: n = a, c, g or t
<220> FEATURE:
<221> NAME/KEY: unsure
<222> LOCATION: (489)
<223> OTHER INFORMATION: n = a, c, g or t

<400> SEQUENCE: 43
gacctagact acaacggcgt tgaagaccaa tcctcaacac aagaacaaat atcaaccaat    60

```
ctcaacacca tgtaccggca actggtgtca agttcaaaga ctccaacgct cttcttcggt      120
agcccttacc gtgcaggaga agatagtgat cccggtggtg gcactgtgga gaacattcct      180
cacggtccgg tccatatatg gaccggtgat aacacacaac ctaactttga ggacatgggg      240
actctctatt ctgctgctag agaccctatt ttctattctc accacgctaa tgtggataga      300
atgtggtcca tatggaaaac tcttngagga aagagagtga catcaaagac cctgattgtt      360
ggaatctggg ttctttctac gatgagaaca agaatcntgt cgtgtgaggt naggattgtc      420
tngtactaga agcttgantg ntaccaaatg atntgtccgt ggnaaancta gccaaancgg      480
tttcgangng gtcaaga                                                     497
```

<210> SEQ ID NO 44
<211> LENGTH: 112
<212> TYPE: PRT
<213> ORGANISM: Glycine max
<220> FEATURE:
<221> NAME/KEY: UNSURE
<222> LOCATION: (109)
<223> OTHER INFORMATION: Xaa = any amino acid

<400> SEQUENCE: 44

```
Asp Leu Asp Tyr Asn Gly Val Glu Asp Gln Ser Ser Thr Gln Glu Gln
 1               5                  10                  15

Ile Ser Thr Asn Leu Asn Thr Met Tyr Arg Gln Leu Val Ser Ser Ser
            20                  25                  30

Lys Thr Pro Thr Leu Phe Phe Gly Ser Pro Tyr Arg Ala Gly Glu Asp
        35                  40                  45

Ser Asp Pro Gly Gly Gly Thr Val Glu Asn Ile Pro His Gly Pro Val
    50                  55                  60

His Ile Trp Thr Gly Asp Asn Thr Gln Pro Asn Phe Glu Asp Met Gly
65                  70                  75                  80

Thr Leu Tyr Ser Ala Ala Arg Asp Pro Ile Phe Tyr Ser His His Ala
                85                  90                  95

Asn Val Asp Arg Met Trp Ser Ile Trp Lys Thr Leu Xaa Gly Lys Arg
            100                 105                 110
```

<210> SEQ ID NO 45
<211> LENGTH: 713
<212> TYPE: DNA
<213> ORGANISM: Glycine max
<220> FEATURE:
<221> NAME/KEY: unsure
<222> LOCATION: (579)
<223> OTHER INFORMATION: n = a, c, g or t
<220> FEATURE:
<221> NAME/KEY: unsure
<222> LOCATION: (618)
<223> OTHER INFORMATION: n = a, c, g or t

<400> SEQUENCE: 45

```
ggtccctcct gaacctgtct gcatccattc ccatttcttc ttccgtatgc atgttcccac       60
cgtctaaaaa acctagcaaa gcaacaaaac ggcgtcatgc ttgggaagta gcatgcaatg      120
gtaaccctag aaataggagg gacattctga tcggccttgg aggactctat ggtgctacaa      180
caagtctcac aagtaacaac actggttctg catttggtgc ttcattgtcg cctccagatc      240
caactaactg cgttcaaccg gacccagaaa aagacccttt ttgccccacca ccccccttcaa      300 agactacgag ctccctccac acgatgacaa gacattaccc cttcgaatta gaccaagctg      360
ctcatttggt cactgatgat tacatagcca agtacgagga agccgtgagg cgcatgcaag      420
```

```
accttccacc tgatgatcct cgcagtttca tgcaacaagc caatgtccac cgtgcctact      480
gcgatggtcc cggctatatc aaaagggttc gctgactaca agcttgacgt tcacggtcct      540
ggatatcctt ccctgggacg ctggtactcc atttctaana aaaacctggg aagatgatcg      600
atgacccact tcgctctncg ttttggaacg ggacaatccc gccggatgag atcctcccat      660
ttcacaagac aaattcactc tctacgacga acacaagaat acgttaatgt taa             713
```

<210> SEQ ID NO 46
<211> LENGTH: 162
<212> TYPE: PRT
<213> ORGANISM: Glycine max

<400> SEQUENCE: 46

```
Ser Leu Leu Asn Leu Ser Ala Ser Ile Pro Ile Ser Ser Ser Val Cys
  1               5                  10                  15

Met Phe Pro Pro Ser Lys Lys Pro Ser Lys Ala Thr Lys Arg Arg His
             20                  25                  30

Ala Trp Glu Val Ala Cys Asn Gly Asn Pro Arg Asn Arg Arg Asp Ile
         35                  40                  45

Leu Ile Gly Leu Gly Gly Leu Tyr Gly Ala Thr Thr Ser Leu Thr Ser
 50                  55                  60

Asn Asn Thr Gly Ser Ala Phe Gly Ala Ser Leu Ser Pro Pro Asp Pro
 65                  70                  75                  80

Thr Asn Cys Val Gln Pro Asp Pro Glu Lys Asp Pro Phe Cys Pro Pro
             85                  90                  95

Pro Pro Ser Lys Thr Thr Ser Ser Leu His Thr Met Thr Arg His Tyr
            100                 105                 110

Pro Phe Glu Leu Asp Gln Ala Ala His Leu Val Thr Asp Asp Tyr Ile
        115                 120                 125

Ala Lys Tyr Glu Glu Ala Val Arg Arg Met Gln Asp Leu Pro Pro Asp
        130                 135                 140

Asp Pro Arg Ser Phe Met Gln Gln Ala Asn Val His Arg Ala Tyr Cys
145                 150                 155                 160

Asp Gly
```

US 6,680,185 B1

PLANT POLYPHENOL OXIDASE HOMOLOGS

This application claims the benefit of U.S. Provisional Application No. 60/119,590, filed Feb. 10, 1999.

FIELD OF THE INVENTION

This invention is in the field of plant molecular biology. More specifically, this invention pertains to nucleic acid fragments encoding polyphenol oxidase enzymes in plants and seeds.

BACKGROUND OF THE INVENTION

Polyphenol oxidase (PPO) catalyzes the oxidation of mono- and O-diphenols to O-diquinones. The oxidation of mono- and diphenols, which occurs during fruit ripening and plant wounding, produces and undesirable browning of fruit and vegetable material (Hunt M. D., et al. 1993, *Plant Mol. Biol.* 21(1):59–68). Inhibition of polyphenol oxidase activity would likely prevent the accumulation of the brown discoloration in fruits and may improve flavor. Furthermore, polyphenols function as antioxidants; inhibition of polyphenol oxidase would increase the level of polyphenols in fruits and vegetables and thus add food value.

In plants polyphenol oxidase activity appears to be encoded by a multigene family. For example, in tomato seven nuclear genes have been reported that encode PPO activity (Newman S. M., et al., 1993, *Plant Mol. Biol.* 21(6):1035–1051). The nucleic acid fragments described herein also appear to encode several different PPO enzymes. Based on amino acid homology, seven different PPO types (that share less than 75% similarity at the amino acid level) have been identified in soybean cDNA libraries. Nucleic acid fragments encoding a two types of PPO enzymes from corn and one type of PPO from wheat are also described. The various types of PPO enzymes have been designated A-I.

There is a great deal of interest in identifying the genes that encode proteins involved in polyphenol oxidation in plants. These genes may be used in plant cells to control the oxidation of phenolic compounds that impart discoloration to fruit and vegetables. The genes may also be used to increase the level of antioxidants in fruits and vegetables. Accordingly, the availability of nucleic acid sequences encoding all or a portion of a PPO enzyme would facilitate studies to better understand polyphenol oxidation in plants and provide genetic tools to inhibit or otherwise alter PPO activity which in turn could provide mechanisms to control discoloration in fruits and vegetables and increase the pool of antioxidant compounds in plant cells.

SUMMARY OF THE INVENTION

The present invention relates to isolated polynucleotides comprising a nucleotide sequence encoding a polypeptide of at least 112 amino acids that has at least 80% identity based on the Clustal method of alignment when compared to a polypeptide selected from the group consisting of corn polyphenol oxidase polypeptides of SEQ ID NOs:4, 38 and 42, soybean polyphenol oxidase polypeptides of SEQ ID NOs:6, 24 28, 32, 34, 36 and 44, and a wheat polyphenol oxidase polypeptide of SEQ ID NO: 14. The present invention also relates to an isolated polynucleotide comprising the complement of the nucleotide sequences described above.

The present invention also relates to isolated polynucleotides comprising a nucleotide sequence encoding a polypeptide of at least 163 amino acids that has at least 80% identity based on the Clustal method of alignment when compared to a polypeptide selected from the group consisting of a corn polyphenol oxidase polypeptide of SEQ ID NO:40, and soybean polyphenol oxidase polypeptides of SEQ ID NOs:10 and 20. The present invention also relates to an isolated polynucleotide comprising the complement of the nucleotide sequences described above.

The present invention also relates to isolated polynucleotides comprising a nucleotide sequence encoding a polypeptide of at least 50 amino acids that has at least 80% identity based on the Clustal method of alignment when compared to a polypeptide selected from the group consisting of SEQ ID NOs:2, 8, 12, 16, 18, 22, 30 and 46.

It is preferred that the isolated polynucleotides of the claimed invention consists of a nucleic acid sequence selected from the group consisting of SEQ ID NOs:1, 3, 5, 7, 9, 11, 13,15, 17, 19, 21, 23, 25, 27, 29, 31, 33, 35, 37, 39, 41, 43 and 45 that codes for the polypeptide selected from the group consisting of SEQ ID NOs:2, 4, 6, 8, 10, 12, 14, 16, 18, 20, 22, 24, 26, 28, 30, 32, 34, 36, 38, 40, 42, 44 and 46. The present invention also relates to an isolated polynucleotide comprising a nucleotide sequences of at least one of 40 (preferably at least one of 30, most preferably at least one of 15) contiguous nucleotides derived from a nucleotide sequence selected from the group consisting of SEQ ID NOs:3, 5, 9, 13, 19, 23, 27, 31, 33, 35, 37, 39, 41, and 43 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a polyphenol oxidase polypeptide of at least 112 amino acids comprising at least 80% homology based on the Clustal method of alignment compared to a polypeptide selected from the group consisting of SEQ ID NOs:4, 6, 14, 24, 32, 34, 36, 38, 42 and 44.

The present invention relates to a polyphenol oxidase polypeptide of at least 163 amino acids comprising at least 80% homology based on the Clustal method of alignment compared to a polypeptide selected from the group consisting of SEQ ID NOs:10, 20 and 40.

The present invention also relates to a polypeptide of at least 50 amino acids comprising at least 80% homology based on the Clustal method of alignment compared to a polypeptide selected from the group consisting of SEQ ID NOs:2, 8, 12, 16, 18, 22, 30 and 46.

The present invention relates to a method of selecting an isolated polynucleotide that affects the level of expression of a polyphenol oxidase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a polyphenol oxidase polypeptide in the host cell containing the isolated polynucleotide; and (d) comparing the level of a polyphenol oxidase polypeptide in the host cell containing the isolated polynucleotide with the level of a polyphenol oxidase polypeptide in the host cell that does not contain the isolated polynucleotide.

The present invention relates to a method of obtaining a nucleic acid fragment encoding a substantial portion of a polyphenol oxidase polypeptide gene, preferably a plant polyphenol oxidase polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:3, 5, 9, 13, 19, 23, 27, 31, 33, 35, 37, 39, 41, and 43 and the complement of such nucleotide sequences; and amplifying a nucleic acid fragment (preferably a cDNA inserted in a cloning vector) using the oligonucleotide primer. The amplified nucleic acid fragment will preferably encode a portion of a polyphenol oxidase amino acid sequence.

The present invention also relates to a method of obtaining a nucleic acid fragment encoding all or a substantial portion of the amino acid sequence encoding a polyphenol oxidase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, 11, 13, 15, 17, 19. 21, 23, 25, 27, 19, 31, 33, 35, 37, 39, 41, 43 and 45.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the polyphenol oxidase polynucleotide in an amount sufficient to complement a null mutant to provide a positive selection means. Inhibition of polyphenol oxidase activity would likely prevent the accumulation of the brown discoloration in fruits and may improve flavor.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:3, 9, 13, 19, 27, 31, 33 and amino acid sequences SEQ ID NOs:4, 10, 14, 20, 28, 32 and 34 were determined by further sequence analysis of cDNA clones encoding the amino acid sequences set forth in SEQ ID NOs:2, 8, 12, 16, 18, 22, 26, 30 and 46. Nucleotide SEQ ID NOs:1, 7, 11, 15, 17, 21, 25, 29 and 45 and amino acid SEQ ID NOs:2, 8, 12, 16, 18, 22, 26, 30 and 46 were presented in a U.S. Provisional Application No. 60/119,590, filed Feb. 10, 1999. The sequence descriptions and Sequence Listing attached hereto comply with the rules governing nucleotide and/or amino acid sequence disclosures in patent applications as set forth in 37 C.F.R. §1.821–1.825.

TABLE I

Polyphenol Oxidase Enzymes

| Protein | Clone Designation | SEQ ID NO: (Nucleotide) | SEQ ID NO: (Amino Acid) |
|---|---|---|---|
| Polyphenol Oxidase A | cpi1c.pk001.o22 EST | 1 | 2 |
| Polyphenol Oxidase A | cpi1c.pk001.o22 FIS | 3 | 4 |
| Polyphenol Oxidase A | Contig Composed of: p0083.cldcl92r p0107.cbcau93r | 5 | 6 |
| Polyphenol Oxidase A | Contig composed of: sfl1.pk0041.a9 sfl1.pk0111.b7 sfl1.pk0122.h9 | 7 | 8 |
| Polyphenol Oxidase A | sfl1.pk0111.b7 CGS | 9 | 10 |
| Polyphenol Oxidase A | wlm96.pk0023.a11 EST | 11 | 12 |
| Polyphenol Oxidase A | wlm96.pk0023.a11 CGS | 13 | 14 |
| Polyphenol Oxidase B | Contig composed of: sfl1.pk0074.f6 sfl1.pk132.d21 | 15 | 16 |
| Polyphenol Oxidase B | Contig composed of: sfl1.pk0025.b4 sfl1.pk0095.h1 sfl1.pk133.k3 srr3c.pk003.d19 | 17 | 18 |
| Polyphenol Oxidase B | sfl1.pk133.k3 CGS | 19 | 20 |
| Polyphenol Oxidase B | Contig composed of: sgc7c.pk001.i6 sgc7c.pk001.o2 | 21 | 22 |
| Polyphenol Oxidase C | Contig composed of: sgc6c.pk001.h11 sgc6c.pk001.h13 | 23 | 24 |
| Polyphenol Oxidase D | Contig composed of: sls1c.pk001.i11 sls1c.pk003.l12 sls2c.pk001.e2 | 25 | 26 |
| Polyphenol Oxidase D | sls1c.pk001.i11 CGS | 27 | 28 |
| Polyphenol Oxidase E | Contig composed of: sfl1.pk0057.e9 sfl1.pk0099.a3 sgs4c.pk002.n13 src3c.pk005.d9 srr1c.pk002.j24 | 29 | 30 |
| Polyphenol Oxidase E | src3c.pk005.d9 CGS | 31 | 32 |
| Polyphenol Oxidase F | sfl1.pk126.m8 CGS | 33 | 34 |
| Polyphenol Oxidase G | sfl1.pk0007.c3 CGS | 35 | 36 |
| Polyphenol Oxidase H | Contig composed of: ccs1c.pk002.k13 p0013.csdlu31rb p0013.csdlu31rd p0117.chclp75r | 37 | 38 |

TABLE I-continued

Polyphenol Oxidase Enzymes

| | | SEQ ID NO: | |
|---|---|---|---|
| Protein | Clone Designation | (Nucleo-tide) | (Amino Acid) |
| Polyphenol Oxidase H | Contig composed of: csc1c.pk004.a22 csiln.pk0036.d5 p0016.ctsbd45rc p0016.ctsbd45rf p0016.ctsbw54rb p0018.chssz59rb p0119.cmtnp57r | 39 | 40 |
| Polyphenol Oxidase H | p0097.cqraa41r EST | 41 | 42 |
| Polyphenol Oxidase I | sr1.pk0024.h11 EST | 43 | 44 |
| Polyphenol Oxidase F | sfl1.pk126.m8 EST | 45 | 46 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, 25, 27, 29, 31, 33, 35, 37, 39, 41, 43, 45 or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein. "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 19, 31, 33, 35, 37, 39, 41, 43, 45 and the complement of such nucleotide sequences may be used in methods of selecting an isolated polynucleotide that affects the expression of a polypeptide (polyphenol oxidase) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–1 53) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1 989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys*. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol*. 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning. A Laboratory Manual*; Cold Spring Harbor Laboratory Press: Cold Spring Harbor, 1989 (hereinafter "Maniatis").

Nucleic acid fragments encoding at least a portion of several polyphenol oxidase enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other polyphenol oxidase either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 15, 27, 29, 31, 33, 35, 37, 39, 41, 43, 45 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as polyphenol oxidse) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (polyphenol oxidase).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol*. 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of polyphenol oxidase activity in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression. Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107.065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded polyphenol oxidase enzyme. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis. A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| ccs1c | Corn Callus | ccs1c.pk002.k13 |
| cpi1c | Corn pooled BMS treated with chemicals related to biochemical compound synthesis** | cpi1c.pk001.o22 |
| csc1c | Corn 20-Day Seedling; Germination Under Cold Stress | csc1c.pk004.a22 |
| csi1n | Corn Silk* | csi1n.pk0036.d5 |
| dms2c | African daisy developing seeds | dms2c.pk001.k8 |
| p0013 | | p0013.csdlu31rb |
| | | p0013.csdlu31rd |
| p0016 | Corn Tassel Shoots, Pooled, 0.1–1.4 cm | p0016.ctsbd45rc |
| | | p0016.ctsbd45rf |
| | | p0016.ctsbw54rb |
| p0018 | Corn Seedling After 10 Day Drought, Heat Shocked for 24 Hours, Harvested After Recovery at Normal Growth Conditions for 8 Hours | p0018.chssz59rb |
| p0083 | Corn Whole Kernels 7 Days After Pollination | p0083.cldcl92r |
| p0097 | Corn V9*** Whorl Section (7 cm) From Plant Infected Four Times With European Corn Borer | p0097.cqraa41r |
| p0107 | Corn Whole Kernels 7 Days After Pollination* | p0107.cbcau93r |
| p0117 | Expanding internode: plants sampled @ the V10*** stage. Internodes 5–9 (the upper 4–5 expanding internodes) | p0117.chclp75r |
| p0119 | Corn Stage V12*** Ear Shoot With Husk, Night Harvested* | p0119.cmtnp57r |
| sfl1 | Soybean Immature Flower | sfl1.pk0007.c3 |
| | | sfl1.pk0025.b4 |
| | | sfl1.pk0041.a9 |
| | | sfl1.pk0057.e9 |
| | | sfl1.pk0074.f6 |
| | | sfl1.pk0095.h1 |
| | | sfl1.pk0099.a3 |
| | | sfl1.pk0111.b7 |
| | | sfl1.pk0122.h9 |
| | | sfl1.pk126.m8 |
| | | sfl1.pk132.d21 |
| | | sfl1.pk133.k3 |
| sgc4c | Soybean Cotyledon 14–21 Days After Germination (¼ yellow) | sgs4c.pk002.n13 |
| sgc6c | Soybean Cotyledon 16–26 Days After Germination (all yellow) | sgc6c.pk001.h11 |
| | | sgc6c.pk001.h13 |
| sgc7c | Soybean Cotyledon 18–30 Days After Germination (yellow and wilting) | sgc7c.pk001.i6 |
| | | sgc7c.pk001.o2 |
| sls1c | Soybean Infected With *Sclerotinia sclerotiorum* Mycelium | sls1c.pk001.i11 |
| | | sls1c.pk003.112 |
| sls2c | Soybean Infected With *Sclerotinia sclerotiorum* Mycelium | sls2c.pk001.e2 |
| sr1 | Soybean Root | sr1.pk0024.h11 |
| src3c | Soybean 8 Day Old Root Infected With Cyst Nematode *Heterdera glycenis* | src3c.pk005.d9 |

TABLE 2-continued cDNA Libraries from Corn, Rice, Soybean and Wheat

| Library | Tissue | Clone |
|---|---|---|
| srr1c | Soybean 8-Day-Old Root | srr1c.pk002.j24 |
| srr3c | Soybean 8-Day-Old Root | srr3c.pk003.d19 |
| vs1n | Vernonia Seed* | vs1n.pk0010.d5 |
| wlm96 | Wheat Seedlings 96 Hours After Inoculation With *Erysiphe graminis f.* sp *tritici* | wlm96.pk0023.-a11 |

*These libraries were normalized essentially as described in U.S. Pat. No. 5,482,845, incorporated herein by reference.
**Chemicals used included sorbitol, egosterol, taxifolin, methotrexate, D-mannose, D-glactose, alpha-amino adipic acid, ancymidol
***Corn developmental stages are explained in the publication "How a corn plant develops" from the Iowa State University Coop. Ext. Service Special Report No. 48 reprinted June 1993.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAPT™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding polyphenol oxidase enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Polyphenol Oxidase

The BLASTX search using the EST sequences from clones listed in Table 3 revealed similarity of the polypeptides encoded by the cDNAs to polyphenol oxidase from *Malus domestica* (NCBI Identifier No. gi 1172584), *Vitis vinifera* (NCBI Identifier No. gi 1785613), *Vica faba* (NCBI Identifier No. gi 418754), *Vica faba* (NCBI Identifier No. gi 1172586), Saccharum sp. (NCBI Identifier No. gi 2737882) and *Prunus persica* (NCBI Identifier No. gi 4519437). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to *Malus domestica*, *Vitis vinifera*, *Vica faba*, Saccharum sp. and *Prunus persica* Polyphenol Oxidase

| Clone | Status | BLAST pLog Score |
|---|---|---|
| cpi1c.pk001.o22 | FIS | 70.70 (gi 1172584) |
| Contig Composed of: p0083.cldc192r p0107.cbcau93r | Contig | 27.22 (gi 1785613) |
| sfl1.pk0111.b7 | CGS | >254.00 (gi 1172584) |
| wlm96.pk0023.a11 | CGS | 160.00 (gi 1172584) |
| sfl1.pk133.k3 | CGS | >254.00 (gi 418754) |
| Contig composed of: sgc6c.pk001.h11 sgc6c.pk001.h13 | Contig | 13.40 (gi 1172584) |
| sls1c.pk001.i11 | CGS | >254.00 (gi 418754) |
| src3c.pk005.d9 | CGS | 173.00 (gi 1172586) |
| sfl1.pk126.m8 | CGS | 127.00 (gi 418754) |
| sfl1.pk0007.c3 | CGS | 150.00 (gi 1172584) |
| Contig composed of: ccs1c.pk002.k13 p0013.csdlu31rb p0013.csdlu31rd p0117.chclp75r | Contig | 100.00 (gi 2737882) |
| Contig composed of: csc1c.pk004.a22 csi1n.pk0036.d5 p0016.ctsbd45rc p0016.ctsbd45rf p0016.ctsbw54rb p0018.chssz59rb p0119.cmtnp57r | Contig | >254.00 (gi 2737882) |
| p0097.cqraa41r | EST | 9.04 (gi 2737882) |
| sr1.pk0024.h11 | EST | 56.40 (gi 4519437) |

The data in Table 4 represents a calculation of the percent identity of the amino acid sequences set forth in SEQ ID NOs:4, 6, 10, 14, 20, 24, 28, 32, 34, 36, 38, 40, 42, 44, 46 and 48 and the *Malus domeslica*, *Vitis vinifera*, *Vica faba*, Saccharum sp. and *Prunus persica* sequences.

TABLE 4

Percent Identity of Amino Acid Sequences
Deduced From the Nucleotide Sequences of
cDNA Clones Encoding Polypeptides Homologous
to *Malus domestica, Vitis vinifera,
Vica faba, Saccharum* sp. and
*Prunus persica* Polyphenol Oxidase

| SEQ ID NO. | Percent Identity to |
|---|---|
| 4 | 44% (gi 1172584) |
| 6 | 42% (gi 11785613) |
| 10 | 60% (gi 1172584) |
| 14 | 47% (gi 1172584) |
| 20 | 62% (gi 418754) |
| 24 | 28% (gi 1172584) |
| 28 | 56% (gi 418754) |
| 32 | 46% (gi 1172586) |
| 34 | 37% (gi 418754) |
| 36 | 40% (gi 1172584) |
| 38 | 46% (gi 2737882) |
| 40 | 74% (gi 2737882) |
| 42 | 35% (gi 2737882) |
| 44 | 71% (gi 4519437) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a polyphenol oxidase. These sequences represent the first african daisy, corn, soybean, vernonia and wheat sequences encoding polyphenol oxidase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt. Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having polyphenol oxidase B activity, wherein the polypeptide has an amino acid sequence of at least 80% sequence identity, based on the Clustal V method of alignment, when compared to SEQ ID NO:20, or
   (b) a complement of the nucleotide sequence of (a), wherein the complement and the nucleotide sequence consist of the same number of nucleotides and are 100% complementary.

2. The polynucleotide of claim 1, wherein the amino acid sequence of the polypeptide has at least 85% sequence identity, based on the Clustal V method of alignment, when compared to SEQ ID NO:20.

3. The polynucleotide of claim 1, wherein the amino acid sequence of the polypeptide has at least 90% sequence identity, based on the Clustal V method of alignment, when compared to SEQ ID NO:20.

4. The polynucleotide of claim 1, wherein the amino acid sequence of the polypeptide has at least 95% sequence identity, based on the Clustal V method of alignment, when compared to SEQ ID NO:20.

5. The polynucleotide of claim 1, wherein the amino acid sequence of the polypeptide comprises SEQ ID NO:20.

6. The polynucleotide of claim 1 wherein the nucleotide sequence comprises SEQ ID NO:19.

7. A vector comprising the polynucleotide of claim 1.

8. A recombinant DNA construct comprising the polynucleotide of claim 1 operably linked to at least one regulatory sequence.

9. A method for transforming a cell, comprising transforming a cell with the polynucleotide of claim 1.

10. A cell comprising the recombinant DNA construct of claim 8.

11. A method for production of a polypeptide having polyphenol oxidase B activity comprising the steps of cultivating the cell of claim 10 under conditions that allow for the synthesis of the polypeptide and isolating the polypeptide from the cultivated cells, from the culture medium, or from both the cultivated cells and the culture medium.

* * * * *

UNITED STATES PATENT AND TRADEMARK OFFICE
CERTIFICATE OF CORRECTION

PATENT NO. : 6,680,185 B1 Page 1 of 1
DATED : January 20, 2004
INVENTOR(S) : Cahoon Rebecca E. and Miao Guo-Hua It is certified that error appears in the above-identified patent and that said Letters Patent is hereby corrected as shown below:

Title page,
Item [75], Inventors, delete "Saverio Carl Falco, Arden, DE (US); Anthony J. Kinney, Wilmington, DE (US)"

Signed and Sealed this

Twenty-eighth Day of September, 2004

JON W. DUDAS
*Director of the United States Patent and Trademark Office*